(12) United States Patent
Warren et al.

(10) Patent No.: US 9,567,353 B2
(45) Date of Patent: Feb. 14, 2017

(54) SOL-GEL PRECURSORS AND PRODUCTS THEREOF

(75) Inventors: Scott C. Warren, Washington, DC (US); Francis J. DiSalvo, Jr., Ithaca, NY (US); Ulrich B. Weisner, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 12/440,516

(22) PCT Filed: Sep. 10, 2007

(86) PCT No.: PCT/US2007/078069
§ 371 (c)(1),
(2), (4) Date: Jun. 17, 2009

(87) PCT Pub. No.: WO2008/031108
PCT Pub. Date: Mar. 13, 2008

(65) Prior Publication Data
US 2010/0019188 A1    Jan. 28, 2010

Related U.S. Application Data

(60) Provisional application No. 60/825,037, filed on Sep. 8, 2006.

(51) Int. Cl.
| | | |
|---|---|---|
| *H01F 1/00* | (2006.01) | |
| *B01J 13/00* | (2006.01) | |
| *C07F 7/18* | (2006.01) | |

(52) U.S. Cl.
CPC .................. *C07F 7/1836* (2013.01)

(58) Field of Classification Search
None
See application file for complete search history.

(56) References Cited

U.S. PATENT DOCUMENTS

| | | |
|---|---|---|
| 6,277,489 B1 | 8/2001 | Abbot |
| 2003/0143407 A1* | 7/2003 | Yamasaki et al. ............ 428/447 |
| 2003/0230363 A1 | 12/2003 | Sturgill |
| 2005/0074612 A1 | 4/2005 | Eklund et al. |
| 2005/0084464 A1 | 4/2005 | McGrath et al. |
| 2005/0191491 A1 | 9/2005 | Wang |
| 2006/0034924 A1 | 2/2006 | Wyrsta |
| 2006/0118158 A1 | 6/2006 | Zhang |
| 2006/0131238 A1 | 6/2006 | Xu |
| 2006/0134505 A1 | 6/2006 | Wang et al. |

OTHER PUBLICATIONS

Yantasee et al. et al. J. Nanosci. Nanotech., 2005, 5(9), 1537.*
Dong et al. et al. (Materials Chemistry and Physics, 95, 2006, 89-93).*
Warren et al. PMSE Preprints (2006), 95, 380-381.*
Schubert et al. Journal of Sol-Gel Science and Technology, 26, 47-55, 2003.*
Pham, T., et al., Preparation and Characterization of Gold Nanoshells Coated with Self-Assembled Monolayers, American Chemical Society, vol. 18, No. 12, May 17, 2002, pp. 4915-4920.
Collman, Belmont, Brauman, "A Silica-Supported Rhodium Hydroformylation Catalyst: Evidence for Dinuclear Elimination," Journal of the American Chemical Society, 1983, vol. 105, No. 205; pp. 7288-7294.
Cruz-Aguado, Chen, Zhang, Elowe, Brook, Brennan, "Ultrasensitive ATP Detection Using Firefly Luciferase Entrapped in Sugar-Modified Sol-Gel-Derived Silica," Journal of the American Chemical Society, 2004, vol. 126, No. 22; pp. 6878-6879.
Fu, Sa Ferreira, Silva, Carlos, Bermudez, Rocha, "Photoluminescence and Quantum Yields of Urea and Urethane Cross-Linked Nanohybrids Derived from Carboxylic Acid Solvolysis," Chemical Materials, 2004, vol. 16, No. 8; pp. 1507-1516.
Cole-Hamilton, "Homogeneous Catalysis—New Approaches to Catalyst Separation, Recovery, and Recycling," Science, 2003, vol. 299; pp. 1702-1706.
Corriu, "Ceramics and Nanostructures from Molecular Precursors," Angewandte Chemie International Edition, 2000, vol. 39; pp. 1376-1398.

(Continued)

*Primary Examiner* — Yun Qian
(74) *Attorney, Agent, or Firm* — Hodgson Russ LLP

(57) ABSTRACT

The present invention provides a generalizable single-source sol-gel precursor capable of introducing a wide range of functionalities to metal oxides such as silica. The sol-gel precursor facilitates a one-molecule, one-step approach to the synthesis of metal-silica hybrids with combinations of biological, catalytic, magnetic, and optical functionalities. The single-source precursor also provides a flexible route for simultaneously incorporating functional species of many different types. The ligands employed for functionalizing the metal oxides are derived from a library of amino acids, hydroxy acids, or peptides and a silicon alkoxide, allowing many biological functionalities to be built into silica hybrids. The ligands can coordinate with a wide range of metals via a carboxylic acid, thereby allowing direct incorporation of inorganic functionalities from across the periodic table. Using the single-source precursor a wide range of functionalized nanostructures such as monolith structures, mesostructures, multiple metal gradient mesostructures and Stober-type nanoparticles can be synthesized.

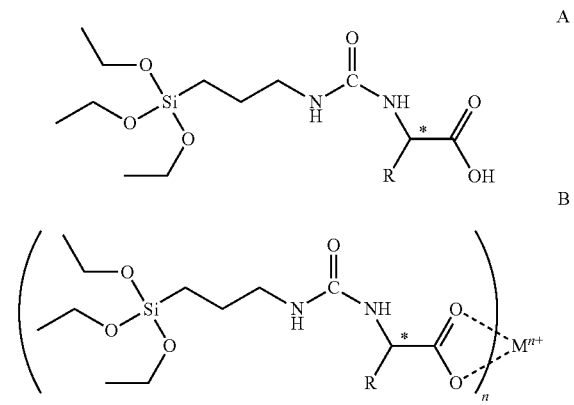

47 Claims, 9 Drawing Sheets

(56) References Cited

OTHER PUBLICATIONS

Katz, Davis, "Molecular imprinting of bulk, microporous silica," Nature, 2000, vol. 403; pp. 286-289.

Dislich, "New Routes to Multicomponent Oxide Glasses," Angewandte Chemie International Edition, 1971, vol. 10, No. 6; pp. 363-434.

Lenaerts, Storms, Mullens, D'Haen, Gorller-Walrand, Binnemans, Driesen, "Thin Films of Highly Luminescent Lanthanide Complexes Covalently Linked to an Organic-Inorganic Hybrid Material via 2-Substituted Imidazo[4,5-f]-1,10-phenanthroline Groups," Chemical Materials, 2005, vol. 17, No. 20; pp. 5194-5201.

Hakeem, Dauce, Leonova, Eden, Shen, Grins, Esmaeilzadeh, "Silicate Glasses with Unprecedented High Nitrogen and Electropositive Metal Contents Obtained by Using Metals as Precursors," Advanced Materials, 2005, vol. 17; pp. 2214-2216.

Minoofar, Hernandez, Chia, Dunn, Zink, Franville, "Placement and Characterization of Pairs of Luminescent Molecules in Spatially Separated Regions of Nanostructured Thin Films," Journal of the American Chemical Society, 2002, vol. 124, No. 48; pp. 14388-14396.

Louloudi, Deligiannakis, Hadjiliadis, "Design and Synthesis of New Biomimetic Materials by Sol-Gel: A CuII(histidine)2 Complex Covalently Bonded on a Silica Matrix," Inorganic Chemistry, 1998, vol. 37, No. 26; pp. 6847-6851.

Yi, Zou, Li, Chen, Tanga, Hea, "Asymmetric epoxidation of a,b-unsaturated ketones catalyzed by silica-grafted poly(L)-leucine catalysts," Tetrahedron Letters, 2005, vol. 46; pp. 5665-5668.

Zheludkevich, Salvado, Ferreira, "Sol-gel coatings for corrosion protection of metals," Journal of Materials Chemistry, 2005, vol. 15; pp. 5099-5111.

Kroger, Lorenz, Brunner, Sumper, "Self-Assembly of Highly Phosphorylated Silaffins and Their Function in Biosilica Morphogenesis," Science Magazine, 2002, vol. 298; pp. 584-586.

Coradin, Allouche, Boissiere, Livage, "Sol-Gel Biopolymer/Silica Nanocomposites in Biotechnology," Current Nanoscience, 2006, vol. 2, No. 3; pp. 219-230.

Cheben, del Monte, Worsfold, Carlsson, Grover, Mackenzie, "A photorefractive organically modified silica glass with high optical gain," Nature, 2000, vol. 408; pp. 64-67.

Mackintosh, "On the Action of Hydrofluoric Acid on Silica and Silicates," Journal of the American Chemical Society, 1886, pp. 210-220.

Hant, Attard, Riddle, Ryan, "Periodic Binary Si:Ti, Si:Al Mixed Macroporous Oxides with Ultrahigh Heteroatom Loading: A Facile Sol-Gel Approach," Chemical Materials, 2005, vol. 17, No. 6; pp. 1434-1440.

Cabrera, El Haskouri, Guillem, Latorre, Beltran-Porter, Beltran-Porter, Marcos, Amoros, "Generalised syntheses of ordered mesoporous oxides: the atrane route," Solid States Sciences, 2002, vol. 2; pp. 405-420.

Kremera, Torres, Dominguez, Mederos, "Structure and thermodynamic stability of lanthanide complexes with amino acids and peptides," Coordination Chemistry Reviews, 2005, vol. 249; pp. 567-590.

Hossain, Mercier, "Intraframework Metal Ion Adsorption in Ligand-Functionalized Mesoporous Silica," Advanced Materials, 2002, vol. 14, No. 15; pp. 1053-1056.

Tacke, Schmid, Merget, "The SiOH-Containing r-Amino Acid HOMe2SiCH2CH(NH2)COOH and Its Immobilization on Silica via an Si—O—Si Linkage," Organometallics, 2005, vol. 24, No. 7; pp. 1780-1783.

Medintz, "Correspondence—Universal Tools for Biomolecular Attachment to Surfaces," Nature Materials, 2006, vol. 5; p. 842.

Tanev, Chlbwe, Pinnavala, "Titanium-containing mesoporous molecular sieves for catalytic oxidation of aromatic compounds," Nature, 1994, vol. 368; pp. 321-323.

Luechinger, Kienhofer, Pirngruber, "Immobilized Complexes of Metals with Amino Acid Ligands—A First Step toward the Development of New Biomimetic Catalysts," Chemical Materials, 2006, vol. 18, No. 5; pp. 1330-1336.

Ryan, Berry, Anderson, Long, Stroud, Cepak, Browning, Rolison, Merzbacher, "Electronic connection to the interior of amesoporous insulator with nanowires of crystalline RuO2," Nature, 2000, vol. 406; pp. 169-172.

Morris, Anderson, Stroud, Merzbacher, Rolison, "Silica Sol as a Nanoglue: Flexible Synthesis of Composite Aerogels," Science, 1999, vol. 284; pp. 622-624.

Green, Le, Grey, Au, Sailor, "White Phosphors from a Silicate-Carboxylate Sol-Gel Precursor That Lack Metal Activator Ions," Science, 1997, vol. 276; pp. 1826-1828.

Sanchez, Lebeau, Chaput, Boilot, "Optical Properties of Functional Hybrid Organic-Inorganic Nanocomposites," Advanced Materials, 2003, vol. 15. No. 22; pp. 1969-1994.

Rozes, Steunou, Fornasieri, Sanchez, "Titanium-Oxo Clusters, Versatile Nanobuilding Blocks for the Design of Advanced Hybrid Materials," Monatshefte fur Chemie Chemical Monthly, 2006, vol. 137; pp. 501-528.

Torma, Peterlik, Bauer, Rupp, Husing, Bernstorff, Steinhart, Goerigk, Schubert, "Mixed Silica Titania Materials Prepared from a Single-Source Sol-Gel Precursor: A Time-Resolved SAXS Study of the Gelation, Aging, Supercritical Drying, and Calcination Processes," Chemical Materials, 2005, vol. 17, No. 12; pp. 3146-3153.

Schubert, "Silica-Based and Transition Metal-Based Inorganic-Organic Hybrid Materials—A Comparison," Journal of Sol-Gel Science and Technology, 2003, vol. 26; pp. 47-55.

Puchberger, Rupp, Bauer, Schubert, "Reaction of metal alkoxides with 3-alkyl-substituted acetylacetone derivatives—coordination vs. hydrodeacylation," New Journal of Chemistry, 2004, vol. 28; pp. 1289-1294.

Numata, Sugiyasu, Hasegawa, Shinkai, "Sol-Gel Reaction Using DNA as a Template: An Attempt Toward Transcription of DNA into Inorganic Materials," Angewandte Chemie International Edition, 2004, vol. 43; pp. 3279-3283.

Stupp, Braun, "Molecular Manipulation of Microstructures: Biomaterials, Ceramics, and Semiconductors," Science, 1997, vol. 277; pp. 1242-1248.

Inagaki, Guan, Ohsuna, Terasaki, "An ordered mesoporous organosilica hybrid material with a crystal-like wall structure," Nature, 2002, vol. 416; pp. 304-307.

Terry, Lugmair, Tilley, "Tris(tert-butoxy)siloxy Complexes as Single-Source Precursors to Homogeneous Zirconia- and Hafnia-Silica Materials. An Alternative to the Sol-Gel Method," Journal of the American Chemical Society, 1997, vol. 119, No. 41; pp. 9745-9756.

Fujdala, Drake, Bell, Tilley, "Atomic Level Control over Surface Species via a Molecular Precursor Approach: Isolated Cu(I) Sites and Cu Nanoparticles Supported on Mesoporous Silica," Journal of the American Chemical Society, 2004, vol. 126, No. 35; pp. 10864-10866.

Zhao, Yan, "Fluorescent enhancement effect in heterometallic terbium-lanthanum hybrid molecular materials obtained by functional bridge grafting to silica network," Journal of Luminescence, 2006, vol. 118; pp. 317-324.

Tan, Wang, Hai, Ye, Yuan, "Development of functionalized fluorescent europium nanoparticles for biolabeling and time-resolved fluorometric applications," Journal of Materials Chemistry, 2004, vol. 14; pp. 2896-2901.

Vinu A. et al. "Recent advances in functionalization of mesoporous silica", Journal of Nanoscience and Nanotechnology, 2005, vol. 5; pp. 347-371.

International Search Report for international application No. PCT/US07/078069 issued by the International Searching Authority mailed on Apr. 30, 2008.

Written Opinion of the International Searching Authority for international application No. PCT/US07/078069 issued by the International Searching Authority mailed on Mar. 10, 2009.

Warren, Perkins, DiSalvo, Weisner, "A generalized precursor for bioorganic-metal-silica hybrids," Angewandte Chemie International Edition, DOI: 10.1002/anie.200123456 (Not yet published).

Riedel, Ralf; Kleebe, Hans-Joachim; Schonfelder, Herbert; Aldinger, Fritz, "A covalent micro/nanocomposite resistant to high-temeprature oxidation," Nature, 1995, vol. 374; pp. 526-528.

(56) References Cited

OTHER PUBLICATIONS

Han, Polarz, Antonietti, "Cyclodextrin-based Porous Silica Materials as in Situ Chemical "Nanoreactors" for the Preparation of Variable Metal-Silica Hybrids," Chemical Materials, 2001, vol. 13, No. 11; pp. 3915-3919.
Vinu, Hossain, Ariga, "Recent Advances in Functionalization of Mesoporous Silica," Journal of Nanoscience and Nanotechnology, 2005, vol. 5; pp. 347-371.
Rottman, Grader, De Hazan, Melchior, Avnir, "Surfactant-Induced Modification of Dopants Reactivity in Sol-Gel Matrixes," Journal of the American Chemical Society, 1999, vol. 121, No. 37; pp. 8533-8543.

\* cited by examiner

SOL-GEL PRECURSORS AND PRODUCTS THEREOF

PRIORITY CLAIM

This application claims priority to U.S. Prov. App. Ser. No. 60/825,037 filed on Sep. 8, 2006, the disclosure of which is hereby incorporated by reference in its entirety.

STATEMENT OF GOVERNMENT RIGHTS

This invention was made with Government support under contract number DE-FG02-03ER46072, awarded by the Department of Energy ("DOE"), and contract number DMR-00799992, awarded by the National Science Foundation ("NSF"). Scott Warren acknowledges support from the Environmental Protection Agency ("EPA") Science to Achieve Results ("STAR") fellowship program from 2004-2007. The Government has certain rights in this invention.

FIELD OF THE INVENTION

The present invention relates to sol-gel precursors and more particularly to sol-gel precursors comprising varying degrees of functionalization.

BACKGROUND

Sol-gel chemistry provides a low temperature route for preparing metal and certain non-metal oxides that are the prevalent materials used in nanoscience and nanotechnology, as well as in biological systems. C. J. Brinker et al., Sol-gel science: the physics and chemistry of sol-gel processing, Academic Press, Boston, 1990. For example, low reactivity, high temperature stability, biocompatibility, tuneable architecture, and ease of synthesis have made silica (SiO2) a prevalent material for end applications, such as catalysis, photonics, and responsive materials. W. Stöber, et al., J. of Colloid and Interface Science 1968, 26, 62. Metal and non-metal oxides such as silica are relatively inert, however, and other types of functionalities must be combined with the silica for use of these hybrids in applications such as catalysis and sensing.

Since the advent of sol-gel chemistry, a primary goal has been to introduce functionality to these relatively inert substrates. To that end, numerous methods to combine substrates with metals, as well as organometallic, organic, and biological molecules have been developed. These functional particles can be added before, during, or after the sol-to-gel transition. However, if the functional species is added before the sol-to-gel transition, it must be compatible with the sol-gel process. Common routes involve the simultaneous hydrolysis and condensation of a multifunctional single-source precursor or several compatible precursors. K. W. Terry et al., J. of the Am. Chem. Soc. 1997, 119, 9745; P. T. Tanev et al., Nature 1994, 368, 321. Achieving similar rates of hydrolysis and condensation is difficult, however, and these routes have not been generalized. Adding the functional species during the sol-to-gel transition can achieve high loadings, but this method limits the architectures to monoliths. C. A. Morris et al., Science 1999, 284, 622. Moreover, although almost any type of species can be added after the sol-to-gel transition via surface functionalization, the loading of the functional species is limited and the process can impede access to micro or mesopores.

Using single-source precursors—that is, adding functionality before the sol-to-gel transition—is, in principle, the easiest way to incorporate functionality while maintaining access to numerous architectures. The simplest method involves adding water and possibly a solvent to the precursor and allowing the sol-gel process to take its course. Numerous precursors, especially those with lanthanides bound via a linker to a silicon alkoxide, have been developed for fluorescence studies C. Sanchez et al., Adv. Materials 2003, 15, 1969. Synthesizing these single source precursors require complex, multistep syntheses, however. P. Lenaerts, et al., Chemistry of Materials 2005, 17, 5194.

Moreover, while a given route may enable incorporation of a particular metal, the method may not be applicable or extendable to many other metals, or materials. Furthermore, existing methods have been unsuccessful in incorporating biological molecules such as amino acids, peptides and proteins, while claiming success in covalently binding only such biological compounds as saccharides to metal oxides (Brennan et al, Ultrasensitive ATP Detection Using Firefly Luciferase Entrapped in Sugar Modified Sol-gel-Derived Silica, JACS, 2004). Existing methods also prevent the simultaneous incorporation of metals and bioorganic molecules. Accordingly, there is a need for a single source, generalizable method to allow the direct incorporation of metals and other materials in the sol-gel process at higher loading levels, a need that the invention disclosed herein satisfies.

SUMMARY OF THE INVENTION

The present invention relates to an improved precursor useful in sol-gel synthesis reactions. In one embodiment, the precursor comprises a cross-linkable molecule including a first metal $M_1$, wherein the first metal is directly bonded to carbon and the cross-linkable molecule is further conjugated to a functional group comprising a carboxylate group and a side chain R, wherein at least one of the oxygen atoms in the carboxylate group is ligated to a H-atom or a second metal $M_2$, and wherein the second metal $M_2$ may be selected from any metal on the periodic table. This type of universal affinity for the second metal $M_2$ makes the precursor useful in a variety of end applications. In the remainder of this text the precursor is therefore also referred to as the "universal ligand" precursor, or alternately the "universal metal ligand complex." Generally, the universal ligand precursor is an all-encompassing term that can refer to sol-gel precursors in which the carboxylate group is ligated to either a H-atom or a second metal $M_2$, whereas the universal metal ligand complex specifically refers to sol-gel precursors in which the carboxylate group is ligated to a second metal $M_2$. In another embodiment, the precursor comprises a cross-linkable molecule including a first metal $M_1$, wherein the first metal is directly bonded to carbon and the cross-linkable molecule is further conjugated to at least one of an organic, bioorganic or organometallic functional group, each of which comprises a carboxylate group and a side chain R wherein at least one of the oxygen atoms in the carboxylate group is ligated to hydrogen or a second metal $M_2$. Preferably, the functional group is a hydroxy acid, amino acid, peptide or protein functional group.

In one embodiment, a method comprises the steps of providing a cross-linkable molecule comprising a first metal $M_1$, reacting the cross-linkable molecule with a compound comprising a carboxylate group to functionalize the cross-linkable molecule and subjecting the functionalized cross-linkable molecule to hydrolysis and condensation reactions. In this embodiment, the carboxylate group is ligated to a H-atom such that the universal ligand precursor has a carboxylic acid group. In another embodiment, a metal acetate comprising a second metal $M_2$ may be reacted with the universal ligand precursor of the above embodiment prior to the hydrolysis and condensation reactions such that carboxylate group is ligated to $M_2$.

Through these precursors, many functionalized nanostructures, including, but not limited to functionalized monolithic structures, hybrid thin films, spin-coated thin films, mesostructures, multiple metal mesostructured gradient films, metal percolation networks, Stöber-type nanoparticles (Stöber-type C-dots), block copolymer-nanoparticle hybrids, can be produced with functionalizations not previously available. The precursors of the invention also allow for the production of a novel nanostructure, a multiple metal gradient mesostructure ("MMGM"), not previously reported. In one embodiment, a mesostructured gradient film comprises a cross-linked matrix comprising a first molecule, wherein the cross-linked matrix further comprises a repeating pattern of at least one of a plurality of pores and a second molecule distinct from the first molecule. The typical size of the pores and second molecule is between 1.0 nm and 500.0 nm, more particularly, between 5.0 and 200.0 nanometers. The second molecule may include, but is not limited to, a distinct surfactant or surfactant aggregation, or a distinct polymer or polymer aggregation. The film also comprises a first metal within the film and a second metal within the film different from the first metal wherein there is a decreasing concentration of the first metal $M_1$ and a corresponding increasing concentration of the second metal $M_2$ across a length of the film. The second metal may be present in an amount between about 5.0% and 90.0% by weight of the precursor, preferably between about 20% and 80%, and more preferably between about 35% and 55%.

In another embodiment, a method for producing a mesostructured gradient film comprises providing a first cross-linkable precursor functionalized with a first metal $M_1$ and a second cross-linkable precursor functionalized with a second metal $M_2$, providing at least one solution comprising at least one of a block co-polymer and a surfactant, separately subjecting each of the first and second cross-linkable precursors to hydrolysis and condensation reactions to recover first and second partially cross-linkable sols, separately combining each of the first and second partially cross-linkable sols with the at least one solution comprising at least one of the block co-polymer and surfactant, thereby recovering first and second modified hybrid sols after the separately combining step, and allowing the first and second modified hybrid sols to diffuse into each other, thereby recovering a gradient film in which the first and second modified hybrid sols are cross-linked. A modified hybrid sol simply comprises a partially cross-linkable sol in combination with a block co-polymer and/or a surfactant. Optionally, the recovered film may be calcined to yield a plurality of nanoparticles, at least one of which comprises at least one of a metal alloy or intermetallic compound of the first and second metals. In addition, the modified sols can be homogenous solutions. The term "metal," as used in connection with the gradient films, includes metals and semi-metals listed on the periodic table.

Use of the precursor in the sol-gel pathway can be employed to produce a variety of functionalized nanostructures including, but not limited to, functionalized monolithic structures (or monoliths), spin-coated thin films, hybrid thin films, mesostructures, multiple metal mesostructured gradient films, Stöber-type nanoparticles (Stöber-type C-dots), block copolymer-nanoparticle hybrids, metal percolation networks and multiple metal gradient mesostructure ("MMGMs"). Such structures have uses that include, but are not limited to, the preparation of catalysts and catalyst supports, fluorescent imaging and detection, combinatorial screening materials for catalysis, preparation of bioactive/biocompatible surfaces which may be used in therapeutic settings, as well as for uses in prosthetics and implants

BRIEF DESCRIPTION OF THE DRAWINGS

FIG. 6 illustrates multiple metal gradient mesostructures.

DETAILED DESCRIPTION

A single source precursor comprises a cross-linkable molecule including a first metal $M_1$, wherein the first metal is directly bonded to carbon and the cross-linkable molecule is further conjugated to a first functional group capable of being conjugated to the first metal $M_1$ and a second functional group comprising a carboxylic acid or a carboxylate group and a side chain R, wherein at least one of the oxygen atoms in the carboxylic acid group is ligated to hydrogen, or at least one of the oxygen atoms in the carboxylate group is ligated to a second metal $M_2$. As used herein, the term "single source precursor" means a cross-linkable molecule or compound that has been functionalized prior to initiation of a cross-linking reaction or being subjected to the hydrolysis and condensation reactions of the sol-gel synthesis pathway. The first metal in the $M_1$ position includes every metal on the periodic table, preferably the metals Ti, Al, Ga, Zn, Cd, Sn, Zr, Pb, and the semi-metals Bi, Si, Ge, As and Te. The second metal in the $M_2$ position includes every metal on the periodic table, preferably the metals Ag, Bi, Co, Cr, Cu, Er, Eu, Gd, In, Mg, Mn, Mo, Pb, Pd, Pt, Rh, Sr, Y, and Zn and the semimetals B, Si, Ge, As, Sb, Te, and Po. In addition, a virtually limitless range of other functional groups may be incorporated as part of the precursor including, but not limited to, organic groups, bioorganic groups, as well as organo-metallic groups. The organic groups include, but are not limited to, carboxylic acids, hydroxy acids (both synthetic and naturally occurring), azide acids, isocyanate acids, isothiocyanate acids, thiol acids, maleimide acids, aldehyde acids, and polyesters. The bioorganic groups include, but are not limited to, amino acids, hydroxy acids, peptides, peptide fragments, and proteins. Amino acids include, but are not limited to, chiral amino acids, racemic mixtures of amino acids, alpha, beta, gamma, and higher amino acids, and naturally occurring and synthetic amino acids. Hydroxy acids include, but are not limited to, glycolic acid, lactic acid, L-mandelic acid, and synthetic hydroxy acids, such as 2-hydroxy-3-methylbutyric acid or 2,2-dimethyl-3-hydroxybutyric acid. To that end, the precursor, in one embodiment can be considered universal, which means that any metal functionality and most semimetal functionalities can be incorporated as part of the molecule and that any of the aforementioned functional groups, including amino acid or peptide based molecules in the above-mentioned classes, can be directly incorporated as part of the precursor.

Figure 1A:
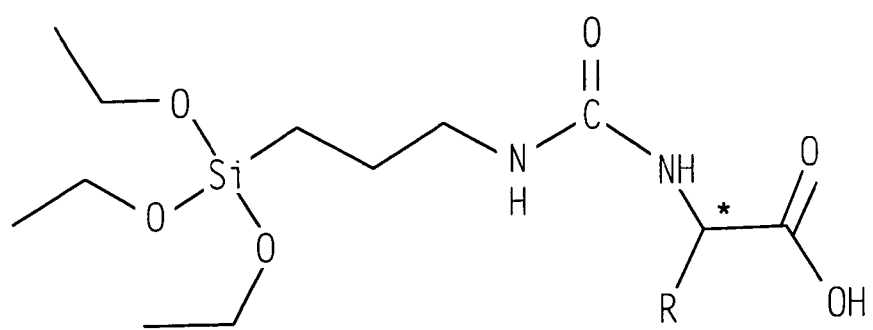
FIG. 1(a) and (b) depict embodiments of the sol-gel precursor in which the metal $M_1$ is Si, the cross-linkable molecule is ICPTS, and the first functional group is an amino acid.
Figure 1B:
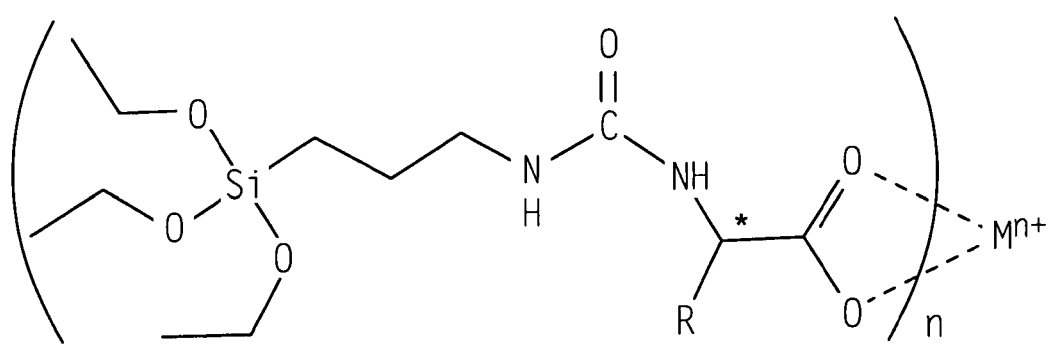
FIG. 1(b) shows the sol-gel precursor ligated to a metal $M_2$.

Embodiments of the sol-gel precursor are shown in FIGS. 1(a) and (b). In this specific embodiment, the metal $M_1$ is Si, the cross-linkable molecule is ICPTS, and the first functional group is an amino acid. The carboxylate group in FIG. 1(a) is bound to a H-atom. FIG. 1(b) shows the sol-gel precursor ligated to a metal $M_2$.

The constituents of the sol-gel precursor may, of course, vary. Suitable first metals $M_1$ include all metals on the periodic table, preferably the metals Ti, Al, Ga, Zn, Cd, Sn, Zr, Pb, and the semi-metals Bi, Si, Ge, As and Te. The molecule comprising a carboxylic acid, side chain R, and a functional group capable of coupling to the molecule containing $M_1$ may be any one of the following: an amino acid, a peptide, a hydroxy acid or a polyester- or, more generally, a molecule containing a carboxylic acid and a second functional group including but not limited to an amine, alcohol, azide, isocyanate, isothiocyanate, thiol, maleimide, and alkyne. The R group can be chosen independently of the first two functional groups. For instance, in glycine, R=H while in isoleucine, R=sec-butyl. $M_2$ may comprise any metal or most semimetals listed on the periodic table, preferably the metals Ag, Co, Cr, Cu, Er, Eu, Gd, In, Mg, Mn, Mo, Pb, Pd, Pt, Rh, Sr, Y, and Zn, and the semimetals Bi, Si, Ge, As, Sb and Te.

The precursor exhibits various advantageous properties. In one embodiment, the precursor comprises a relatively high degree of organic material, on the order of between about 10% and about 100% and more particularly between about 40% and about 90%. The degree of organic material is determined by a comparison of the atomic masses of the organic components (C, H, N, O, S, etc.) and the atomic masses of the inorganic components ($M_1$, $M_2$). As discussed herein, with appropriate solvent selection, precursors comprising high degrees of organic material undergo cross-linking more rapidly during sol-gel synthesis. In another embodiment, the molecule comprising a carboxylic acid, a second functional group, and R group also comprises a chiral portion, designated by an asterisk "*" in the images above. The dotted lines bonding the second metal $M_2$ to the oxygen atom represent coordinate covalent bonds.

The solubility, melting point and viscosity of the precursor are adjustable. A parameter highly relevant to these properties is the size of the side chain R in the functional group. In the absence of a side chain (such as in glycine, where R=H), each oxygen of the carboxylic acid group bridges several atoms of $M_2$, rather than binding solely to a single atom $M_2$. When a sterically hindering side chain is added, bridging is minimized and solubility is enhanced. Sterically hindering side chains include, but are not restricted to, alkyl side-chains, preferably alkyl side chains comprising a benzyl, methyl, ethyl, butyl or t-butyl derivative. The size and location of the side chain also influences the melting point. The larger and more flexible the chain, the lower the melting point. For example, typical maximum solubilities of these single source precursors in a solvent such as tetrahydrofuran ("THF") or dimethyl sulfoxide ("DMSO") can be tuned from 0.1 g of precursor to 1.0 g of solvent up to being soluble in any ratio (miscible) in these solvents. Melting points can be controlled within a broad range depending on the side chain R. For R=$CH_3$, melting points are above 100° C., while for R=$C_4H_9$, melting points are below room temperature. In another embodiment, the side chain R, can comprise functional groups including, but not limited to, a therapeutic agent, a peptide, a polymer, an alcohol, an amine, a nanoparticle and a fluorescent dye.

Precursor Generation: The precursor may be synthesized in various ways. In one embodiment, a cross-linkable molecule comprising a first metal $M_1$ bonded directly to carbon is combined with a molecule comprising a carboxylic group, in the presence of a solvent. The reaction product may be used as the single-source precursor. Optionally, a second step, comprising the addition of a compound comprising a second metal $M_2$ to the reaction product follows. The metal based compound typically comprises this second metal $M_2$ and one or more anionic ligands, with each ligand comprising a single negative charge or, if the ligand is multidentate, each ligating component of the single ligand comprising a single negative charge associated with it. For example, a metal with a single bidentate ligand would have two ligating components, each with a single negative charge formally associated with it. Depending on the needs of the user, $M_1$ and $M_2$ may be the same or different. The product obtained after the second step may also be employed as the single-source precursor. An embodiment of this synthesis of the sol-gel precursor is described by reaction pathway (a) disclosed herein. In another embodiment, the compound comprising the second metal $M_2$ is first combined with a molecule containing a carboxylic group in the presence of a solvent. To the reaction product of this first step, a cross-linkable molecule comprising a first metal $M_1$ bonded directly to carbon is added to form the single-source sol-gel precursor. An embodiment of this synthesis of the sol-gel precursor is described by reaction pathway (b) disclosed herein.

Beyond variation of the metal $M_2$ (that is, any metal on the periodic table and most semimetals) and the molecule containing the carboxylic acid (e.g., amino acid, peptide, and so on) mentioned herein, the cross-linkable molecule containing $M_1$ and the compound comprising $M_2$ can be varied as well. The cross-linkable molecule may be any metal or semimetal alkoxide that is also bonded to a carbon which is, in turn, bonded to a functional group that can undergo a cross-linking reaction with the molecule containing the carboxylic acid. Suitable examples include, but are not limited to 3-isocyanatopropyltriethoxysilane ("ICPTS"), 3-mercaptopropyl triethoxysilane ("MPTS"), isothiocyanatopropyltriethyoxysilane ("ITCPTS") and 3-aminopropyltriethoxysilane ("APTS"). Other suitable examples include derivatives of the above-mentioned molecules in which varying numbers of methylene ($CH_2$) units link the silane with the cross-linking functional group. For example, the two groups may be linked by methyl, ethyl, propyl, butyl, pentyl, hexyl, and higher alkyl or phenyl segments. The alkyl or mixed alkyl-phenyl groups may be linear or branched and may also contain ether functional groups. The metal or semimetal based compound containing $M_2$ may have ligands including but not limited to acetates, alkoxides, nitrates, or halides.

As stated herein, the functional molecule may be an amino acid, peptide, hydroxy acid, polyester, azide acid, isocyanate acid, isothiocyanate acid, thiol acid, maleimide acid, or aldehyde acid. As further stated herein, examples of amino acids include chiral amino acids, racemic mixtures of amino acids, alpha, beta, gamma, and higher amino acids, and naturally occurring and synthetic amino acids; hydroxy acids include glycolic acid, D-lactic acid, L-lactic acid, D-mandelic acid, L-mandelic acid, 2-hydroxy-3-methylbutyric acid or 2,2-dimethyl-3-hydroxybutyric acid and naturally occurring and synthetic hydroxy acids. Peptides are another example of the broad classes of molecules that can be incorporated into these single source precursors. For example, DiProtin A, a peptide sequence (Il-Pro-Ile) that inhibits entry of HIV into cells may also be incorporated. The R group allows further functionalization of the precursor. For example, R may be a therapeutic agent, another peptide or polymer, an alcohol, an amine, a fluorescent dye and even a nanoparticle.

Figure 9:
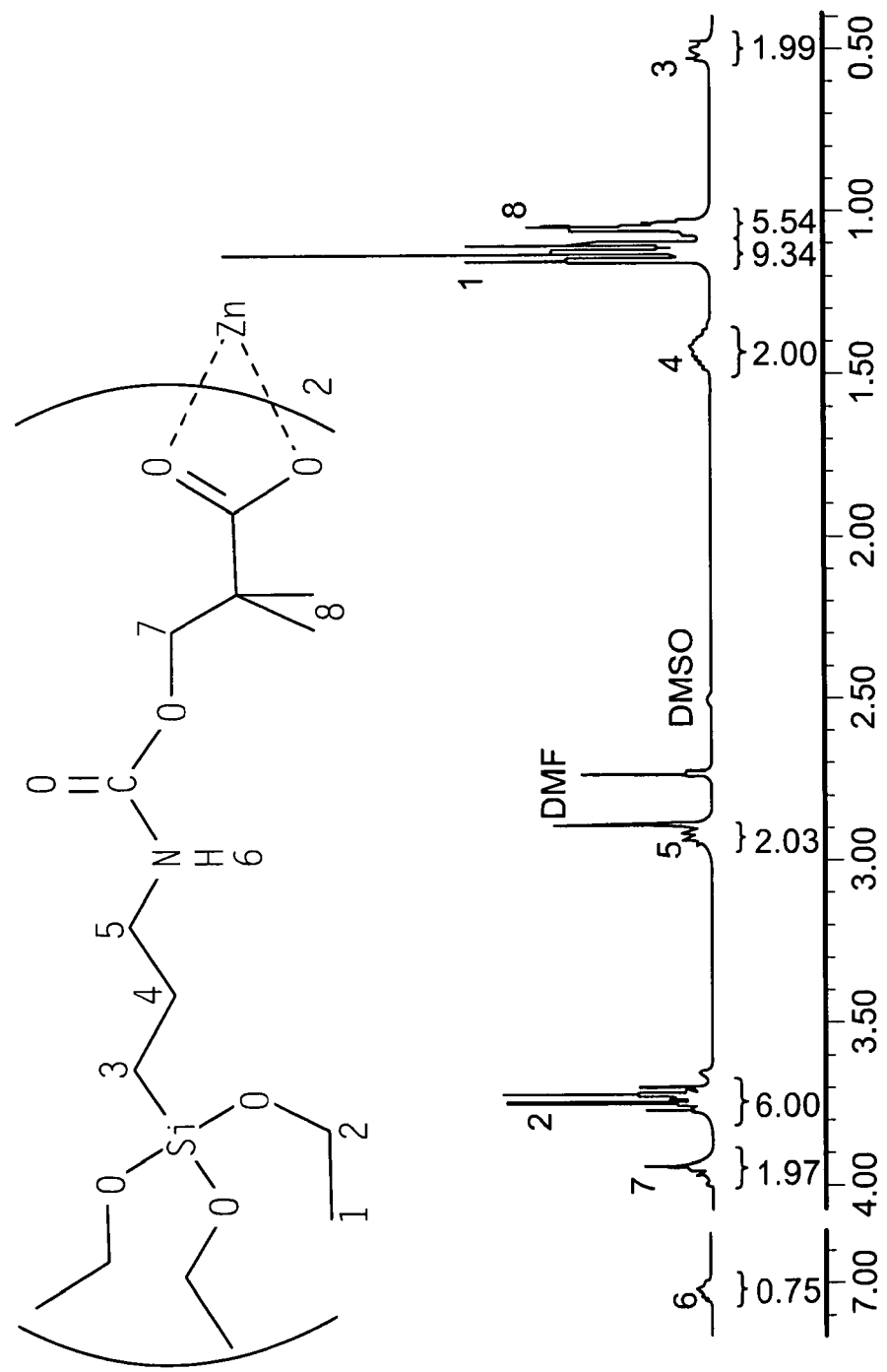
FIG. 9 is a $^1$H NMR showing the purity of a zinc-universal ligand molecule. All peaks appear in the expected locations and ratios, showing that the synthesis was accomplished in very high yield, in this case nearly 100% yield.

The reactants are combined to form precursor products that are homogeneous, clear liquids or solids, which can be immediately used as single-source precursors for sol-gel reactions. The precursors are generated in high yield, typically between 50% and 100%, more particularly between about 60% and about 99%, and even more particularly between about 80% and 98%. For instance, in FIG. 9, a $^1H$ NMR showing the purity of a zinc-universal ligand molecule, all peaks appear in the expected locations and ratios showing that the synthesis was accomplished in very high yield, in this case nearly 100% yield.

The relative proportions of each reactant are generally as follows. The metal alkoxide is provided in an amount between about 0.100 mol and about 0.150 mol. The metal complex comprising the second metal $M_2$ and anionic ligands of unit negative charge, such as metal acetate, is present in an amount between about 0.100/n mol and about 0.150/n mol, where "n" is the oxidation state of the metal. The amounts described above are intended only to suggest typical ratios that have been employed, as these reactions have and can be altered to larger and smaller scale reactions, as needed. Two exemplary reaction pathways are shown below.

Reaction pathway (a) illustrates functionalization of ICPTS (comprising a first semi-metal Si) through complete or partial dissolution of an amino acid, peptide or hydroxy acid in the presence of the solvent N,N-dimethylformamide ("DMF") to yield one embodiment of the precursor of the present invention, followed by incorporation of a second metal $M_2$ through addition of a metal acetate to yield another embodiment of the precursor.

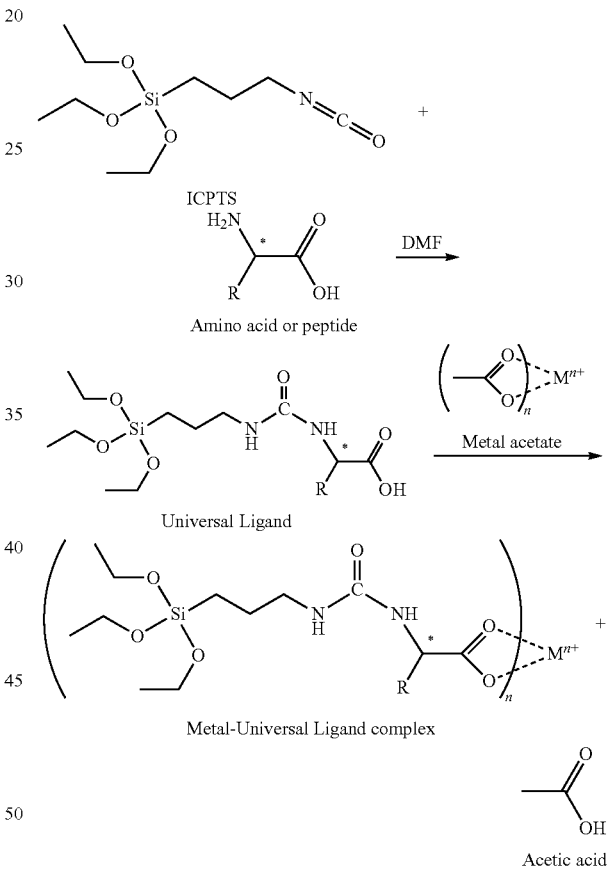

In the first step of the reaction depicted in (a), a side reaction that may occur is the free carboxylic acid of the "Universal Ligand" precursor undergoing a substitution reaction for an ethoxide ligand on the silicon, generating ethanol (this is in equilibrium with the ICPTS to form a urethane linkage). However, NMR shows that the extent to which this occurs is small (<22%). Because of this side reaction, if equimolar amounts of amino acid and ICPTS were added, the excess amino acid can be removed by filtration. When peptides were used instead of amino acids, side reactions were not observed by NMR. It also bears noting that less soluble amino acids, such as alpha amino acids, often rely on heating at temperatures as high as 80° C.

to complete the reaction in a few hours. Reaction with more soluble amino acids (beta and higher) proceed readily at room temperature.

In the second step, upon addition of the metal or semimetal acetate comprising the metal or semi-metal $M_2$, the reaction is subjected to conditions of high vacuum (typically between 0.05 and 1.0 mbar) and heated to as high as 100° C., depending on how labile the acetate is. This allows rapid removal of the acetic acid and DMF, and pushes the equilibrium from the side products back to the precursor (as drawn in pathway (a)), and thus affords the product, the metal-or-semimetal-precursor complex. The quantity of metal or semimetal acetate is based on the amount of amino acid, hydroxy acid, or peptide rather than on the amount of ICPTS in order to allow complete ligand exchange.

Reaction pathway (b) illustrates a second route to generate the single-source precursor, relying on the combination of a metal or semimetal acetate and a hydroxy acid or polyester in the presence of the same solvent DMF, followed by addition of the metal alkoxide ICPTS.

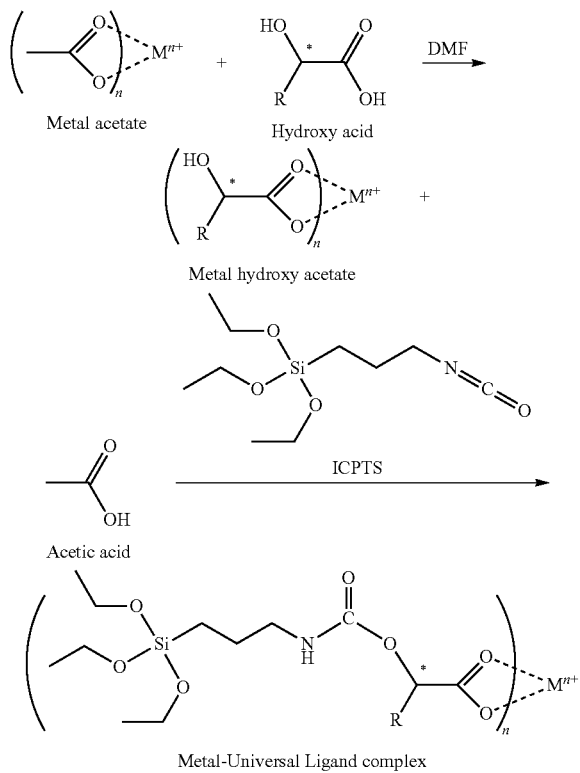

This route typically avoids the side reactions discussed above. The first reaction forms a metal or semimetal hydroxy acetate in quantitative yield, and subsequent reaction with ICPTS also proceeds nearly quantitatively to generate a urethane linkage between the isocyanate of ICPTS and the alcohol of the metal or semimetal hydroxy acetate. No side products could be detected by NMR, and these products were also homogeneous, clear liquids or solids. Thus, the precursor is functionalized prior to sol-gel treatment.

Sol-Gel Pathway: Once the functionalized precursor has been generated, a sol-gel synthesis pathway, in some instances, comprising a single step, may be initiated. A cross-linking reaction that fixes the addition of water, a solvent, an acid or base to the precursor, whereby the precursor is subjected to hydrolysis and condensation, begins the process. The reaction typically proceeds relatively quickly, on average between 20.0 minutes and 100.0 minutes, more particularly between 30.0 and 45.0 minutes. When solvent is employed to initiate cross-linking, excess solvent may thereafter be removed through evaporation. An optional heating step may also be employed. Typically, the temperature employed is between about 20° C. and about 200° C., preferably between about 50° C. and about 150° C.

These single-source precursors can also be combined with other sol-gel precursors to produce materials with a broader composition window. For example, by adding varying amounts of a tetraethylorthosilicate ("TEOS") sol-gel precursor to the universal ligand-metal complex, the Si:$M_2$ ratio can be tuned for specific applications. This is not limited solely to TEOS; this has also been applied to other sol-gel precursors including, but not limited to, 3-glycidyloxypropyltriethoxysilane (glymo) with aluminum sec-butoxide.

Use of the precursor in the sol-gel pathway can be employed to produce a variety of functionalized nanostructures including, but not limited to, functionalized monolithic structures (or monoliths), spin-coated thin films, hybrid thin films, mesostructures, multiple metal mesostructured gradient films, Stöber-type nanoparticles (Stöber-type C-dots), block copolymer-nanoparticle hybrids, metal percolation networks and multiple metal gradient mesostructure ("MMGMs"). The MMGMs are novel structures which are synthesized as such because the various metal universal ligand precursors used have similar rates of hydrolysis and condensation, which allows them to be blended in novel ways. In particular, addition of water to the single-source precursor of the invention via the hydrolysis step allows bulk monolithic materials to grow, whereas spin coating of these materials creates thin films. In general, thin films are those structures that are less than about 1000.0 nm in thickness, whereas monoliths are those structures that are greater than about 1000.0 nm. The addition of the precursors to a block copolymer or surfactant allows mesostructure hybrids to be produced. Subsequent calcination of these hybrids yields porous metal-or-semimetal-rich compounds with well-defined pore sizes. Calcination can proceed at temperatures ranging between about room temperature and 1100° C., preferably between about 50° C. and 800° C. Diffusion of two precursors comprising different first and second metals into one another produces monolithic films containing a gradient in metal concentration of the two metals. When block copolymers are incorporated to these gradient films, calcination produces multiple metal gradient mesostructures. Calcination of these materials produces metal- or semimetal-rich particles with layers containing metal, metal oxide, metal silicide, semimetal, or semimetal oxide nanoparticles. Incorporation of an amino acid, hydroxyl acid or peptide allows multiple biological functionalities, while incorporation of chiral versions of the foregoing materials allows optical properties to be built into the materials, such as the ability to rotate light.

Figure 2:
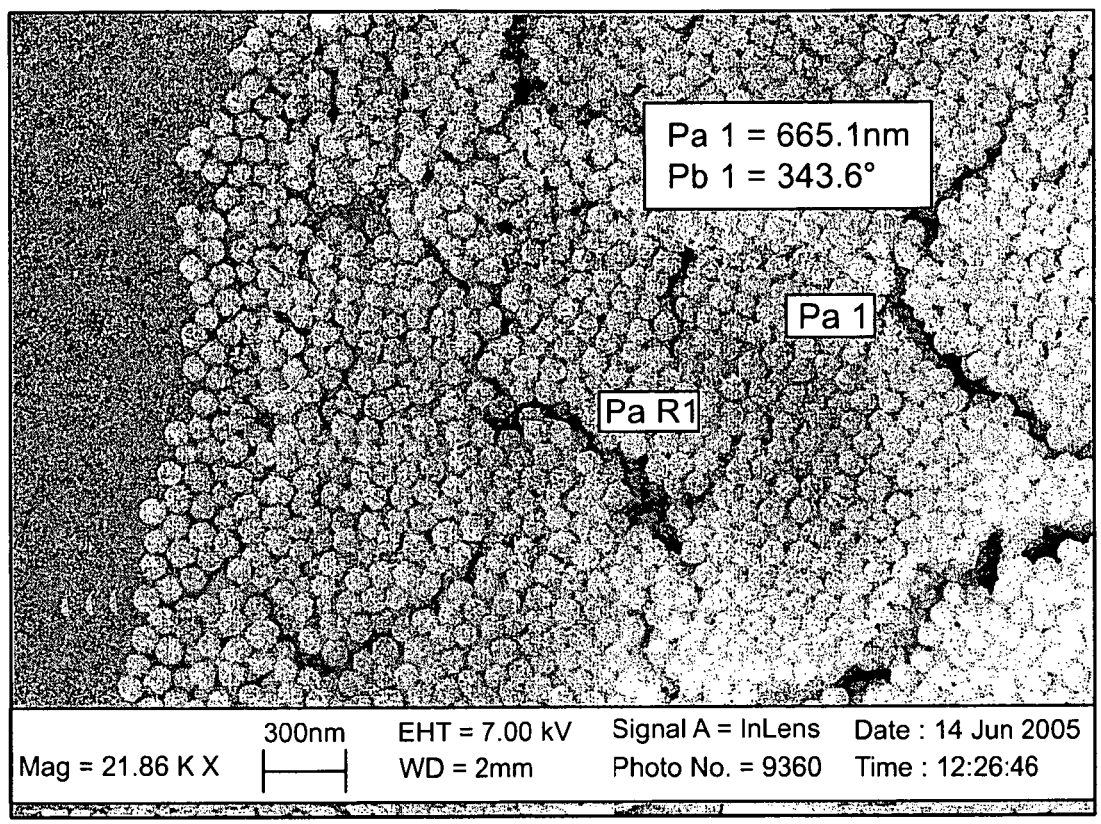
FIG. 2 is a TEM of Stöber-type C-dots prepared in accordance with another embodiment of the present invention. The precursor complex can be used for introducing high loadings of metals into silica-based nanoparticles comprising fluorescent dyes, common referred to as C-dots. Here, a europium-isoleucine-based precursor was incorporated into the core of ~180 nm C-dots.

Addition of the precursors to Stober-type nanoparticles produces well-defined particles in which the universal ligand, specifically the metal-universal ligand complex, has been incorporated. Stober-type nanoparticles are generally silica nanoparticles prepared by the known Stober procedure (J. Colloid and Interface Sci., 26 62-69 (1968)). Using the Stober method besides homogeneous particles core-shell silica nanoparticles can be synthesized in which the core may have a different composition than the shell. For example, in this way one can prepare fluorescent core-shell silica nanoparticles in which the core comprises one or multiple organic dyes covalently attached to the silica network and is encapsulated by a pure silica shell. These particles are also known as C dots. If the shell contains a second organic dye that is able to detect the presence of an analyte, than the particles are referred to as C dot sensors and may be used to monitor, e.g., physiological parameters like pH, metal status or redox, status through ratiometric sensing. The metal-Universal Ligand can be added to the Stober particle during the initial stage of growth (in which case the metal-Universal Ligand complex is incorporated into the core of the final particle) or during the final stage of growth (in which case the metal-Universal Ligand complex is incorporated into a shell of the final particle). FIG. 2 depicts a TEM of Stöber-type C-dots in which a europium-isoleucine-based precursor was incorporated into the core of ~180 nm C-dots. The universal ligand of the invention can be used in the synthesis or modification of any Stöber-type particles. Such Stöber-type particles include, but are not limited to, nanoparticles that comprise a metal-oxide-based core, a polymeric core, a fluorescent material core, a core comprising a magnetic or superparagmagnetic component, or those with a plurality of pores. The Stöber-type particles include those with multifunctional architectures, for example, a core which can optionally contain a functionality such as a magnetic or fluorescent component, a shell which can be made to have a range of useful thicknesses and surface properties, such as a smooth monolithic surface or a highly porous surface, and which surface can be further physically or chemically modified with any additional functional groups and/or ligands. Thus, for example, the Stöber-type particles may have a core comprising one or more photoluminescent dyes or a core of superparagmagnetic material, such as nano-sized iron oxide or other magnetic alloys or oxides. The particles may be further functionalized with any suitable functional group and/or ligand that may be positioned on particle surfaces for various purposes such as a smooth monolithic surface or a highly porous surface. The functional groups and/or ligands may be therapeutic in nature, for example, with antibodies or therapeutic agents to identify and treat disease states or conditions, or may be ligands for particle stabilization against aggregation or to prevent other moieties from sticking on the particle surface like proteins. The ligands may comprise at least one of a polymer and an oligomer selected from the group consisting of a cell component, a biopolymer, a synthetic polymer, an antigen, an antibody, a receptor, a hapten, an enzyme, a hormone, a chemical compound, a pathogen, a toxi, and combinations thereof.

Figure 4:
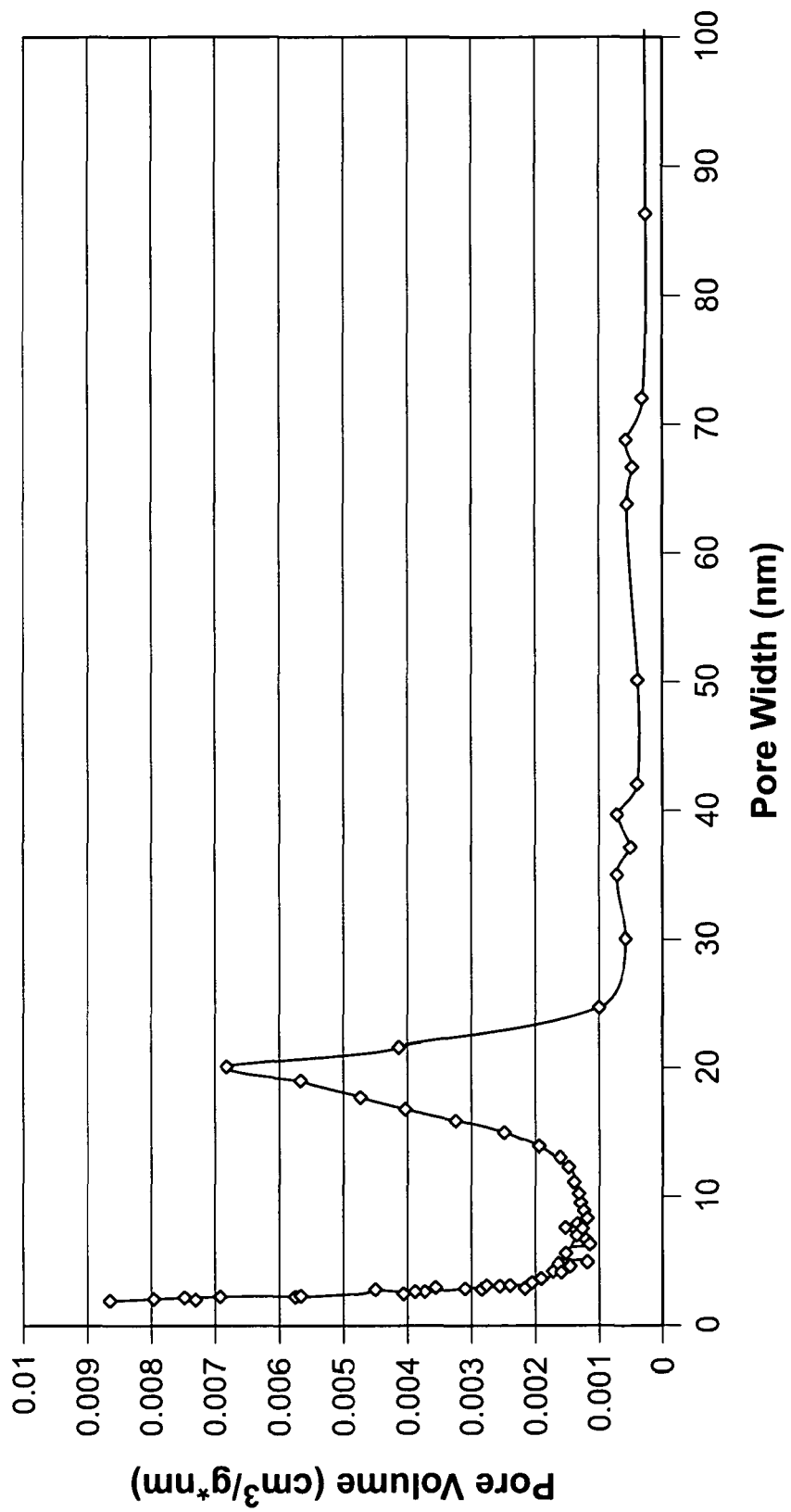
FIG. 4 illustrates nitrogen adsorption/desorption measurements to reveal that mesoporous materials can be made from the precursors of the present invention. Here, a copper-isoleucine-based metal precursor complex was mixed with a poly(isoprene-block-ethylene oxide) block copolymer (PI-b-PEO) and silica and alumina precursors, glymo and aluminum-sec-butoxide. This copper-rich film retains nm pores after calcination.

Methods for producing the foregoing end products through use of the precursor in the sol-gel pathway is described below in the Examples. As shown in FIG. 4, the pores of these functionalized products remain accessible and interconnected. The reason for this is that post-synthesis functionalization of these materials, which often blocks the pores in sol-gel materials, is unnecessary here (though it may be carried out depending on the circumstances). These materials have mesopores of variable diameter; the pore diameter of these end products is typically between 3.0 mm and 150.00 mm and more particularly, between 10.0 nm and 80.0 nm. In addition, these materials have numerous microspores, which are typically less than 3.0 in diameter.

Metal or semimetal loadings in the sol-gel materials derived from the metal-universal ligand complex can range between 5% to about 90%, preferably between about 20% to about 80%, more preferably between about 35% to about 55%. Thus, sol-gel materials derived from the metal-universal ligand complex have exceptionally high metal or semimetal loadings. For example, in the instance where a heavy metal with a valance of 1 is used, such as cesium or thallium, the cesium loading in the as-made final materials will be as high as about 55.0 wt %; in those instances, when clusters of metals or semimetals are used, the upper loading of the metal can be as high as 90%. In contrast, when a metal such as Lithium is used (in a non-clustered form), the lithium loading in the as-made final materials will be as low as 5%.

Figure 6A:
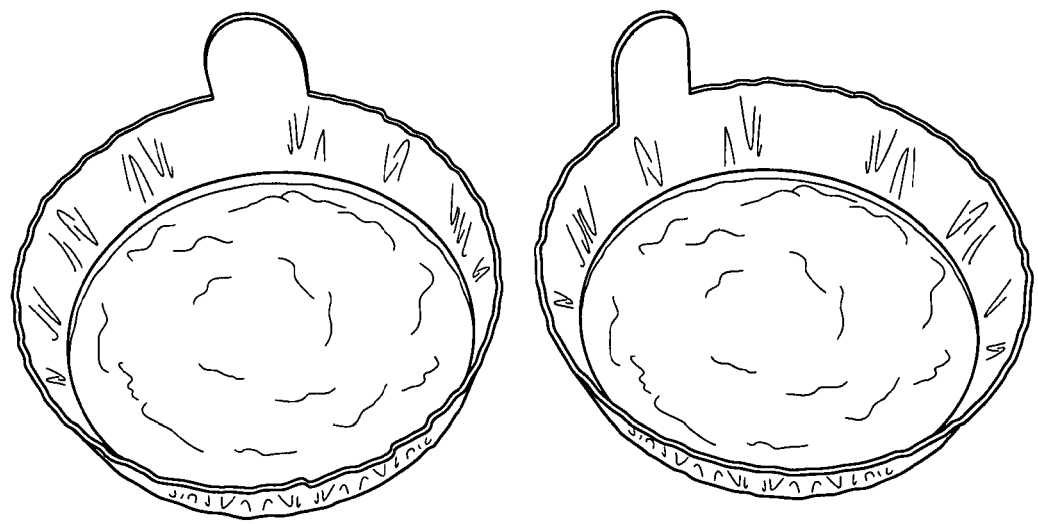
FIG. 6(a) illustrates individual hybrid films of poly(isoprene-block-ethylene oxide) (PI-b-PEO) with a copper-lactic-acid and cobalt-2-hydroxyethyl-3-methylbutyric acid-based hybrids.
Figure 6B:
FIG. 6(b) illustrates a multiple metal gradient mesostructure, made by pouring the copper and cobalt solutions into the same dish and allowing diffusion to make a gradient and mix the two components.

A unique composition enabled by the precursors is a multiple metal gradient mesostructure ("MMGM"). These MMGM's are made by mixing partially hydrolyzed and condensed solutions of precursor-metal or precursors semimetal complexes before the precursors have fully cross-linked. This provides a route to generate hybrid materials with metal or semimetal compositions that vary across the film. For example, pouring partially hydrolyzed and condensed copper and cobalt-based precursor complexes into the same container allow the solutions to diffuse into one another. This generates a decreasing concentration in copper and an increasing concentration in cobalt as one moves across a generated film from left to right (shown in FIGS. 6($a$) and ($b$)). This can be applied to several (not just two) metal precursors, generating composition spread with numerous elements. Subsequent calcination of these materials can produce metal or metal oxide nanoparticles with compositions and phases reflecting the local composition in the gradient.

The end-product of the sol-gel synthesis pathway may be used in a variety of applications. They may be used as catalyst supports or combinatorial screening materials for catalysis (e.g., MMGM's could allow a combinatorial spread of nanoparticles to be synthesized on a metal oxide matrix, such as silica). When the end-product comprises peptides, it may be employed as a prosthetic or implant.

Another unique functionalized structure enabled by the precursors is a bicontinuous percolation network comprising metal and silica ($SiO_2$), or alternately metal oxide and silica. This class of materials is prepared in several steps. In the first step, a film is cast of a partially hydrolyzed and condensed solution of metal-Universal Ligand complex (where $M_1$ is the semi-metal Si, and $M_2$ is the metal of choice for the bicontinuous percolation network) with a second metal precursor, where the metal in this second metal precursor can be the same metal or a different metal from the metal $M_2$ in the metal-Universal Ligand complex. The second metal precursor may be one of highly soluble organometallic complexes such as carboxylates, nitrates, halides, sulfates, chlorates, phosphates, alkenes, dienes, phosphines, sulfides, thiols, and amines, preferably carboxylates, and more preferably the carboxylates 2-ethylhexanoate, 2-methoxyacetate, 2-(2-methoxy)ethoxyacetate, 2-(2-{methoxy}ethoxy)ethoxyacetate or 2-{2-[2-methoxy]ethoxy}ethoxy)ethoxyacetate. After heating the film at 50.0° C., the film is largely cross-linked and the second metal precursor is distributed homogenously throughout the film. In the second step, the film is heated in air to a temperature between 350.0° C. and 700.0° C. This decomposes the film into a composite consisting of silica and metal (if the metal is platinum, gold, or silver) or silica and metal oxide (if the metal is any metal besides platinum, gold, or silver). In this latter case, a third step is taken. The silica-metal oxide composite is then heated under the flow of a reducing gas, such as a hydrogen-forming gas, or carbon monoxide. The composite is typically heated at a temperature between about room temperature and about 1100.0° C., preferably between about 50.0° C. and 800.0° C. This third step reduces the metal oxide to a metal, producing a silica-metal composite. In this way, a metal-silica percolation network is produced in which both the metal and the silica form continuous networks throughout the material. The material is electrically conductive. In a final step, the metal-silica composite can be etched with a solution that dissolves the silica, such as an aqueous solution of sodium hydroxide or a solution of hydrofluoric acid. This removes the silica, leaving behind a percolation network of metal and a percolation network of pores. The material is highly porous and electrically conductive.

Figure 10:
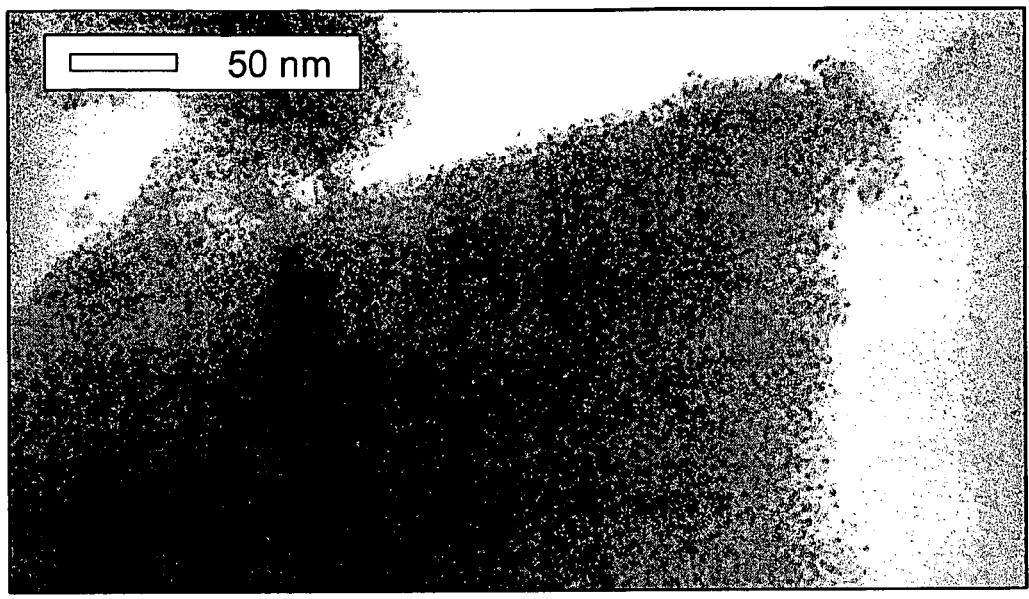
FIG. 10 is a TEM image of a Pd-silica composite synthesized by casting a film of a palladium-Universal Ligand complex without incorporating a second metal precursor.
Figure 11:
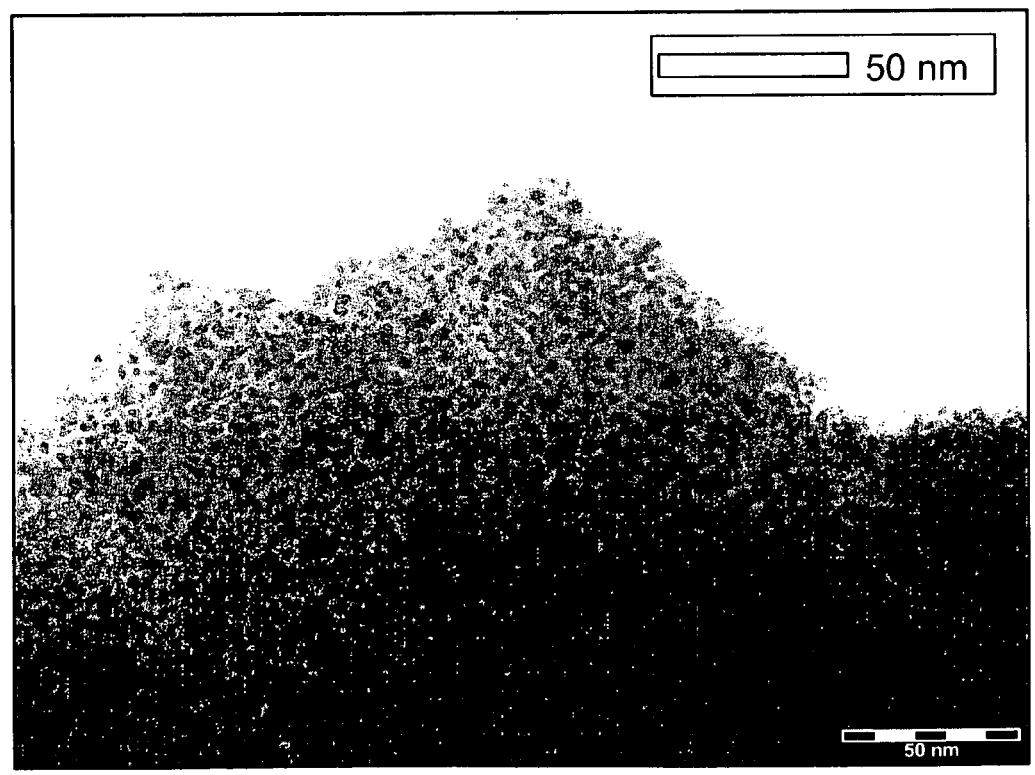
FIG. 11 is a TEM image of a Pd-silica composite synthesized by casting a film of a palladium-Universal Ligand complex in the presence of a second palladium complex, palladium (II) 2-(2-methoxy)ethoxyacetate.

A Palladium-Silica composite on the way towards a percolation network is depicted by the TEM image in FIG. 10. This material was synthesized by casting a film of a palladium-universal ligand complex without incorporating a second metal precursor. The film was calcined in air, followed by heating under forming gas. The dark grey dots in the TEM represent the palladium which is dispersed in the light grey matrix, silica. Yet another palladium-silica composite even closer to the percolation network is depicted by the TEM image in FIG. 11. This material was synthesized by casting a film of a palladium-universal ligand complex in the presence of a second palladium complex, palladium (II) 2-(2-methoxy)ethoxyacetate, where the palladium precursors were mixed in a 1:1 molar ratio. The TEM image shows a material where both the palladium and silica are very close to the percolation threshold.

In another embodiment, the precursors of the invention may be used to produce metal nanoparticle containing hybrid thin films or hybrid nanoparticles suitable for use in optical enhancements, in particular, those thin mesoporous films or Stober-type silica nanoparticles containing dense assemblies of metal nanoparticles. Such structures may easily be prepared by synthesis routes employing the universal ligands of the invention disclosed herein. For example, it is known that molecules in the vicinity of metal nanoparticles like silver or gold exhibit what is referred to as "surface enhanced Raman scattering" ("SERS"). Similarly, it is also known that in the vicinity of metal nanoparticles, optical absorption and emission spectra of fluorescent molecules are greatly enhanced. It is currently believed that these enhancements are caused by surface plasmon resonances, i.e., are due to local electromagnetic field enhancements provided by the nanoparticles. Thin mesoporous films or Stöber-type silica nanoparticles prepared with the use of the universal ligands of the invention can serve as substrates for the deposition of organic molecules exhibiting such optical enhancements.

As mentioned herein, Stöber-type particles (also known as C-dots) can be further modified by the metal-universal ligand complex. C-dots are generally core-shell nanoparticles prepared by the known Stober procedure (J. Colloid and Interface Sci., 26 62-69 (1968)). Moreover, the universal ligand of the invention can be used to modify any core-shell particle.

In one such case, the surface of pre-formed particles can be modified by reaction of the metal-universal ligand complex or universal ligand complex onto the Stöber particles' surface. This allows further modification of the particles' properties. In one such instance, the metal-universal ligand complex allows a biologically relevant species, such as a peptide, amino acid, or hydroxy acid to be covalently bound to the C-dots' surface. This imparts biological properties to the C-dots, allowing the C-dots to interface and interact with other amino acids, hydroxy acids, peptides, proteins, and more generally, components of biological systems.

Additionally, it is known that presence of peptides can modify the catalytic behavior of metals. A unique composition enabled by the metal-Universal Ligand complex is the adsorption of the ligand onto a c-dot surface wherein the peptide can modify the catalytic properties of the metal $M_2$ that is bound to the peptides. Anchoring the metal-universal Ligand complex onto the surface of a C-dot allows a unique composition to be created in which the modified C-dot has combined properties of fluorescence, sensing, biological interfacing, and catalysis.

A further embodiment of such combined fluorescence, sensing, biological interfacing, and catalysis properties can be achieved by the direct incorporation of the metal-Universal Ligand complex into the C-dot. As described in Example 2(f) in the "examples" section herein, the metal-universal ligand complex can be incorporated directly into the core of a C-dot. Additionally, the metal-universal ligand complex can be incorporated into the shell of a C-dot. Or the metal-universal ligand complex can be incorporated into both the shell and the core of a C-dot. In yet another embodiment, different metal-universal ligand complexes can be incorporated into the core and the shell of a C-dot. If the C-dot is also mesoporous, then much of the metal-Universal Ligand that has been incorporated into the c-dot will be accessible via the mesopores. In such an embodiment, the metal-universal ligand complex will be available for fluorescence, sensing, biological interfacing, and catalysis.

When fluorescent species (dyes, molecules, nanoparticles, etc.) are near metal surfaces, Surface Enhanced Raman Scattering (SERS) or enhanced absorption and emission can occur. In this process, the electric field from the metal surface greatly enhances the Raman scattering or absorption/emission. Using the above-described techniques, the metal-universal ligand can be incorporated into C-dots or exclusively onto their surfaces, or both. In any circumstance, the resulting composition can be subjected to a mild heat treatment (calcination) or exposure to ultraviolet light which can decompose the metal complex into metal nanoparticles while retaining the fluorescence activity from, for example, a dye that is incorporated into the C-dots. Conversely, microporous or mesoporous silica nanoparticles with metal nanoparticles obtained as described above can first be synthesized and a fluorescent dye can subsequently be immobilized onto the particle surface or into an additional thin silica shell on top of the primary particle. Such techniques may employ any metal or semi-metal in the periodic table that can be incorporated into the metal-universal ligand complex, preferably precious metals including, but not limited to, silver, gold and platinum. For instance, in one embodiment, silver that is incorporated into c-dots can be converted into silver nanoparticles either by a mild heat treatment (<80° C.) or by exposure of the material to ultraviolet light (365 nm for 1 day). This produces a high density of silver metal nanoparticles within the C-dots, resulting in a greatly enhanced SERS or absorption/emission of a fluorescent dye. This same technique may also be employed with gold or any other metal or semimetal that can be incorporated into the metal-Universal ligand complex.

EXAMPLES

The present invention is illustrated, but in no way limited by the following examples. Examples 1(a)-(c) illustrate synthesis of two embodiments of the precursor of the present invention. Examples 2(1a)-2(f), illustrate use of the precursor in the sol-gel pathway. Example 3 depicts in tabular form some successful combinations of amino acids and metals, and shows that the universal ligand of the invention can be synthesized using a range of both amino acids and metals. Example 4 describes synthesis conditions used for the ligand exchange of acetate for the universal ligand or hydroxy acetate.

For all the experimental conditions described herein, all chemicals were used as received, except as noted below. 3-isocyanatopropyltriethoxysilane ("ICPTS") (Sigma Aldrich, 95%) was distilled under high vacuum prior to use, discarding the first and last fractions. Metal acetates that were sold as hydrates were evacuated several hours at high vacuum to dry the compound. Anhydrous DMF (99.8%) was purchased from Sigma Aldrich and Alfa Aesar. Carboxylic acids were purchased from Sigma Aldrich or Alfa Aesar and were of the highest purity available (typically 99%). DiProtin A was purchased from BaChem. Metal acetates were purchased from a variety of sources, including Sigma Aldrich, Alfa Aesar, DFG Goldsmith, and Gelest. THF was distilled first from sodium and then from n-butyl lithium/diphenylethylene.

In general, Standard Schlenk line techniques were used for the synthesis of the universal ligand. All components of the universal ligand were synthesized and handled under nitrogen, except for the first step of the protocol for hydroxy acids and polyesters, which may be performed in air.

Example 1(a)

Amino Acid-based Precursor Synthesis

In a typical synthesis, 0.05 mol of L-isoleucine (6.56 g) and 0.05 mol of 3-isocyanatopropyltriethoxysilane ("ICPTS") (12.37 g) was combined with 700 mL of anhydrous DMF in a 1-L flask. The reaction was stirred in an oil bath at 80° C. for 12 hours under nitrogen. After cooling to room temperature, unreacted L-isoleucine was removed by pouring the reaction contents through dry Whatman filter paper. Typically, 23% of the L-isoleucine had not reacted. At this point, the precursor could be isolated by distilling the DMF at reduced pressure to afford a clear, slightly viscous liquid. However, for most syntheses, the metal acetate was directly added to the precursor-DMF-solution. An amount of metal acetate ([0.05 (1−0.23)]/n mol, wherein "n" is the oxidation state of the metal) was added to permit complete exchange of the acetate for the precursor. The solution was again heated, gradually increasing the temperature to 80-100° C. while applying dynamic vacuum pressure to distill off acetic acid and subsequently DMF.

The products were clear, viscous liquids or glassy solids that had the same color of the starting metal acetate. The products readily dissolved in a wide range of solvents, although some reacted with chloroform and all underwent alcoholysis or hydrolysis. NMR was typically performed in anhydrous DMSO-$d_6$. NMR spectra were acquired on a Varian Inova at 400 MHz ($^1$H) and 100 MHz ($^{13}$C). Assignment of peaks in the NMR spectra was assisted by ChemDraw Ultra.

Example 1(b)

Hydroxy Acid-based Universal Ligand Synthesis

Metal acetate (e.g. Cu(II) acetate) in an amount of 0.05 mol was added to 0.10 mol of a hydroxy acid, e.g., 2-hydroxy-3-methyl-butanoic acid. 50 mL of DMF was added and vacuum was applied immediately to the solution, and the flask was simultaneously immersed in an oil bath at 80° C. The solution bubbled vigorously for a few minutes as acetic acid was evolved, and, as the solution warmed, DMF was distilled off. This afforded 0.05 mol of a metal hydroxy acetate. To ensure the product was anhydrous, vacuum pressure was applied to the powder for several hours. Next, the metal hydroxy acetate was dissolved in 100 mL of anhydrous DMF and 0.10 mol of ICPTS was added. Stirring the solution at room temperature overnight and vacuum distillation of the DMF afforded the title compound.

Example 1(c)

Peptide-based Precursor Synthesis

In a typical synthesis, equimolar amounts of ICPTS and the peptide were combined. For example, 0.15 mmol of ICPTS and 0.15 mmol of DiProtin-A (a peptide with a Leu-Pro-Leu sequence) were combined in 35 mL of anhydrous DMF. Subsequent addition of an amount of metal acetate ([0.15 (1−0.15)]/n mol, where "n" is the oxidation state of the metal and assuming an 85% yield), was added, and subsequent distillation of the acetic acid and DMF under high vacuum at 50° C. afforded the viscous product.

Example 2(a)

Monolith Formation

Figure 3:
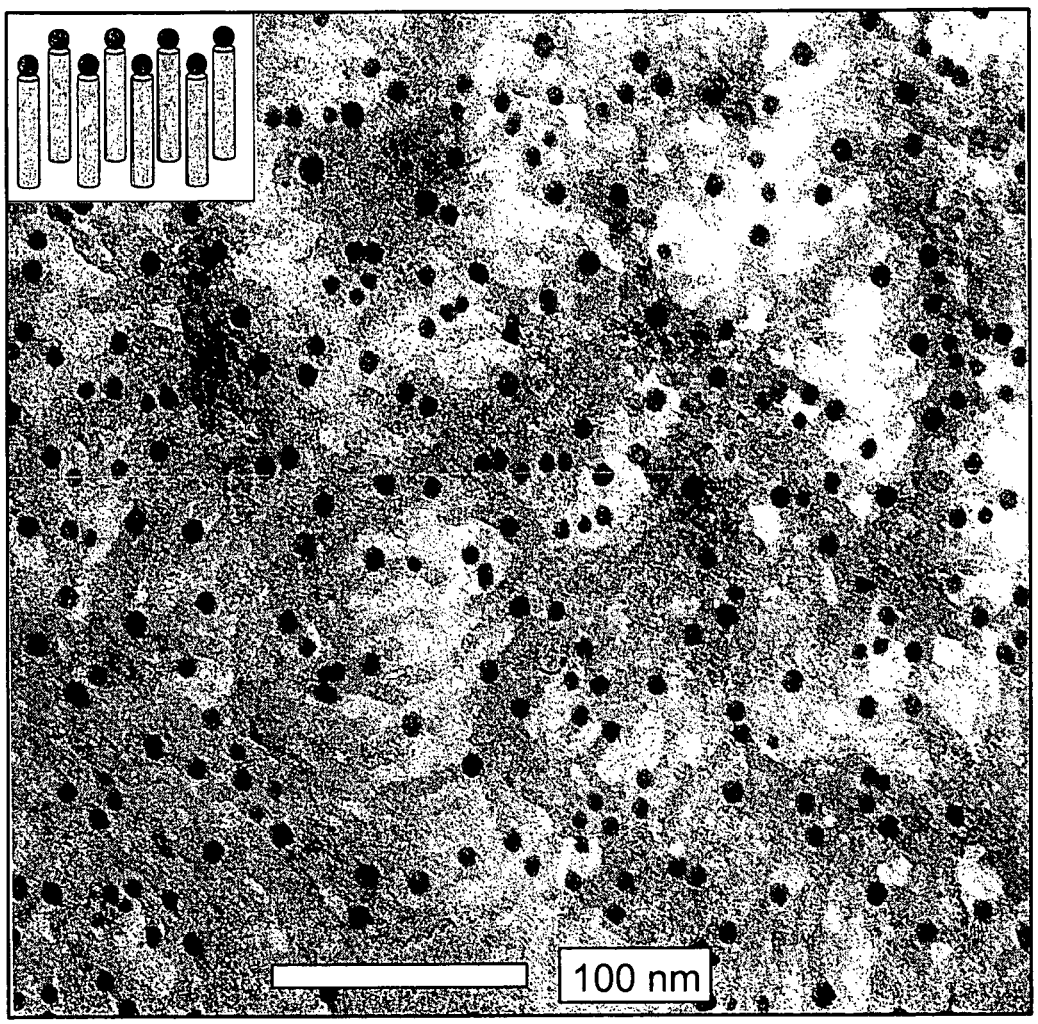
FIG. 3 is a transmission electron microscopy micrograph of a thin film prepared in accordance with one embodiment of the present invention, representing a cylindrical morphology. Upon exposure of one surface of the film to water, bismuth oxide nanoparticles form on the tops of the cylinders, as illustrated in the inset.

Typically, 0.3 g of the metal-precursor complex was dissolved in 2 g of anhydrous THF. After stirring for a few minutes to ensure complete dissolution, pH 9.0 $H_2O$ ($10^{-6}$ M NaOH) was added to initiate hydrolysis and condensation. To ensure complete hydrolysis, a 1:1 molar ratio between alkoxide and water was maintained. After stirring 10 minutes, the film was then cast at 50° C. in an aluminum dish. The dish was covered by a hemispherical glass cover to slow the evaporation of the volatile components. Heating for several hours produced a solid, transparent film. The metal-carboxylic acid linkage in the metal-precursor complex is air or water sensitive in some cases. For water sensitive complexes, such as bismuth, the precursor was dissolved in anhydrous THF, and subsequently stirred in the air for an hour prior to casting the film. Because THF is hygroscopic, a small amount of water was delivered to the precursor and allowed the sol-gel process to occur without hydrolyzing the bismuth. For air sensitive complexes, the entire operation was preformed under nitrogen. FIG. 3 depicts a TEM micrograph of a bismuth-based thin film that shows a cylindrical morphology. Upon exposure of one surface of the film to water, bismuth oxide nanoparticles form on the tops of the cylinders.

Example 2(b)

Mesostructured Hybrid Formation

Figure 8:
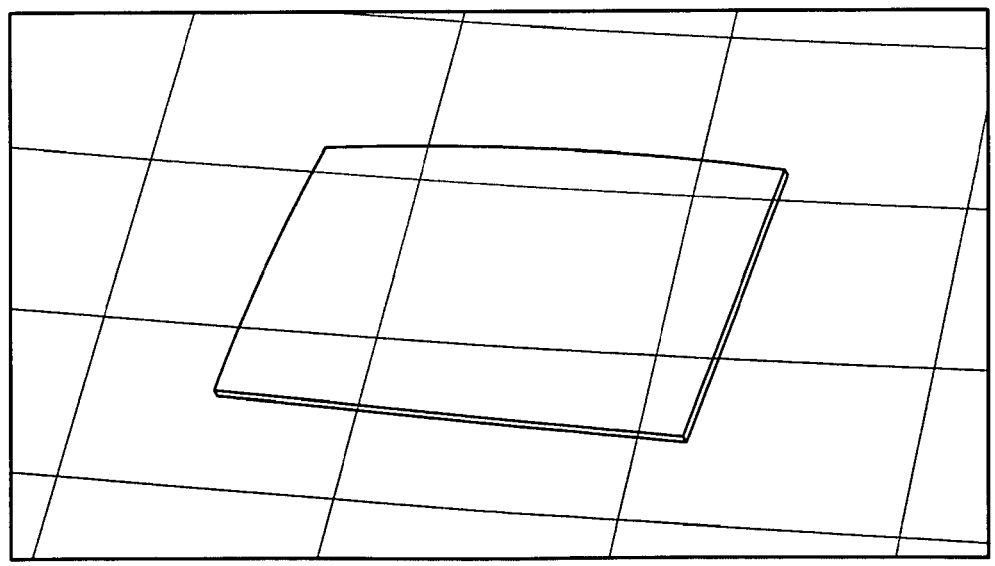
FIG. 8 illustrates a mesostructured film made from the iron-universal ligand complex combined with a block co-polymer, PI-b-PEO. Upon calcination, the resulting silicate is rich in magnetic iron oxide ($\gamma$-$FeO_3$).

The synthesis was identical to the monolith formation, except that the hydrolyzed and condensed sol was added to 0.1 g of poly(isoprene-block-ethylene oxide) (PI-b-PEO) in 2 g of anhydrous THF and stirred for 10 minutes prior to casting the film. Virtually any amino acid, hydroxy acid or peptide can be used for the synthesis of mesostructures and mesostructured block copolymer hybrids. Preferably, the amino acids, hydroxy acids and peptides used are those that are adequately protected, and most those that comprise a sterically hindering and/or chiral R group. For example, one preferred amino acid is L-isoleucine, a chiral amino acid with a sec-butyl side group. The metal-universal ligand complexes formed with this amino acid have extremely high solubility, are easy to handle, produce optically transparent films, and mix well with the Pb-b-PEO block copolymer disclosed herein. FIG. 8 illustrates a mesostructured film made from the iron-universal ligand complex combined with a block co-polymer, PI-b-PEO. Upon calcination, the resulting silicate is rich in magnetic iron oxide ($\gamma$-$FeO_3$).

Example 2(c)

Multiple Metal Mesostructured Gradient Films

Two separate solutions of PI-b-PEO with a specific metal were prepared simultaneously. Each film was cast initially into separate aluminum dishes and the THF was partially evaporated. Once the viscosity had noticeably increased, the two solutions were simultaneously poured into a single aluminum dish to allow the solutions to diffuse into each other. The films were heated at 50° C. for several hours to produce solid films.

Example 2(d)

Mesoporous Silicates

The synthesis was identical to mesostructure formation above, except that tetraethylorthosilicate ("TEOS") was added to decrease the volume fraction of organic material. For example, 0.15 g of TEOS and 0.2 g of metal-precursor complex were dissolved in 2 g of anhydrous THF, which was hydrolyzed and cast as a film with PI-b-PEO, as described above. The film was calcined by heating it to 550° C. for 6 hours at a rate of 1° C./min., with two 3-hour pauses at 250° C. and 350° C.

Example 2(e)

Hybrid Thin Films

Figure 5A:
FIG. 5(a) illustrates a hybrid film made from the hydrolysis and condensation of a yttrium-isoleucine-based metal precursor complex.
Figure 5B:
FIG. 5(b) illustrates a hybrid film made from the hydrolysis and condensation of a copper-isoleucine-based universal ligand and metal complex.
Figure 5C:
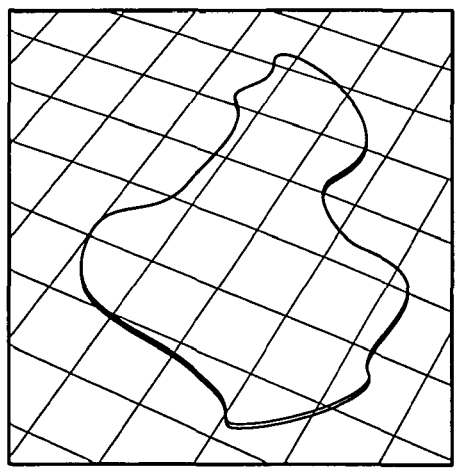
FIG. 5(c) illustrates a block copolymer-hybrid film made from poly(isoprene-block-ethylene oxide) (PI-b-PEO) and a bismuth-isoleucine-based universal ligand and metal complex.

The sol-gel solution was prepared as described for the mesoporous silicates. The solution was then diluted with THF by a factor ranging from 50 (multilayer films) to 450 (monolayer films) and spin-coated by dropping the solution onto a silicon wafer and spin-coating the solution by ramping to 2000 rpm at 250 rpm/s. FIG. 5(*a*) illustrates a hybrid film made from the hydrolysis and condensation of a yttrium-isoleucine-based metal precursor complex. FIG. 5(*b*) illustrates a hybrid film made from the hydrolysis and condensation of a copper-isoleucine-based universal ligand and metal complex. FIG. 5(*c*) illustrates a block copolymer-hybrid film made from poly(isoprene-block-ethylene oxide) (PI-b-PEO) and a bismuth-isoleucine-based universal ligand and metal complex.

Example 2(f)

Stöber-type Particle Formation

A varying amount of metal-universal ligand complex (0-60 mg) was combined with 1.1 mL of TEOS and 5.0 mL of ethanol. A second solution containing 20 mL of 2.0 M $NH_3$ in ethanol, 5.85 mL of water, and 68 mL of ethanol was prepared. The first solution was added to the second, and the solutions were stirred for 12 hours. After this time, 2.675 mL of TEOS was added to the reaction over 10 minutes. Stirring continued for 24 hours, after which the point the particles were isolated from the solvent. These particles could be calcined by heating to 550° C. in air. Any amino acid, peptide, hydroxy acids may be used in the generation of such particles, preferably a hydroxy acid, and most preferably a small hydroxy acid, for example, lactic acid.

Example 3

Some Successful Combinations of Amino Acids and Metals Used to Create the Universal Ligand

TABLE 1

| Carboxylic acid | Metals | Comments |
|---|---|---|
| L-(+)-isoleucine | Ag ($Ag_2tfa_2$), Bi, Co, Cr, Cu, Er, Eu, Gd, In, Mg, Mn, Ni, Pb, Pd, Pt ($Pt_4ac_8$), Sr, Y, Zn | Exhibits high solubility. Product is glassy or is extremely viscous. Used silver trifluoroacetate instead of silver acetate as silver source. |
| $\gamma$-amino butyric acid | Mo ($Mo_2ac_4$), Rh ($Rh_2ac_4$) | Dimeric metal acetates need less sterically demanding ligands to ensure complete ligand exchange. |
| DL-2-aminobutyric acid | Cu, Gd | |
| L-(+)-phenylalanine | Zn | |
| L-(+)-$\alpha$-phenylglycine | Zn | |
| 6-aminohexanoic acid | Pb | Exhibits low solubility. |
| L-valine | Cu, Zn | |
| DL-$\beta$-leucine | Cu | |
| DiprotinA (Ile-Pro-Ile) | Gd | |
| L-(+)-lactic acid | Cu, Zn | |
| 2-hydroxy-3-methylbutyric acid | Co, Cu, Zn | |
| (R)-2-hydroxybutyric acid | Zn | |
| (S)-2-hydroxybutyric acid | Zn | |

TABLE 1-continued

| Carboxylic acid | Metals | Comments |
| --- | --- | --- |
| 2,2-dimethyl-3-hydroxypropionic acid | Mo (Mo$_2$ac$_4$), Zn | Product is Mo$_2$ac$_1$U$_3$, as determined by NMR. |
| L-(+)-mandelic acid | Cu, Zn | |

Figure 7:
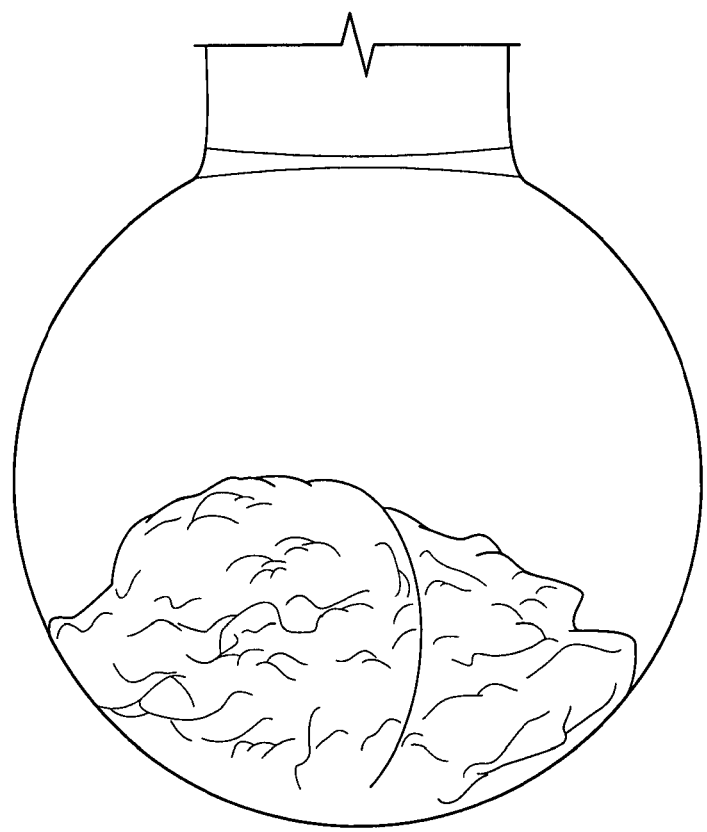
FIG. 7 illustrates a cobalt-universal ligand complex. L-isoleucine-ICPTS was used as the ligand for cobalt.

FIG. 7, for example, shows a cobalt-universal ligand complex in which L-isoleucine-ICPTS was used as the ligand for cobalt.

Example 4

Ligand Exchange Reactions

Ligand exchange of acetate for the Universal Ligand or hydroxy acetate was conducted under dynamic vacuum at varying temperatures. More labile acetates could be exchanged at lower temperatures (e.g., at 20° C.), while less labile acetates required higher temperatures (temperatures up to 150° C.), as described in Table 2. The distillate temperature was typically ~40° C. lower than that of the oil bath temperature. The following table lists the oil bath temperature employed. For the higher temperatures, care was taken to increase the distillation pressure (that is, closer to atmospheric pressure) to prevent the premature distillation of the DMF prior to ligand exchange.

The ligand exchange and DMF distillation were performed using a short path distillation head with vacuum tubing connecting the distillation head to a vacuum/nitrogen port of a vacuum line. The acetic acid and DMF were typically collected in a flask cooled by liquid nitrogen to prevent the distillate from entering into the vacuum line.

The reaction progress could be gauged by the disappearance of the metal acetate (a solid), which typically had low solubility in DMF. Once the reaction reached an appropriate temperature for ligand exchange, the reaction was typically complete in a few minutes. After distillation, the Universal Ligand complex was connected directly to the vacuum line until the pressure stabilized at 10-2 mbar to complete the removal of all volatile components. This typically required a few hours.

TABLE 2

| Oil Bath Temperatures | Metal Acetate |
| --- | --- |
| 20° C. | Pt |
| 50° C. | Ag |
| 70° C. | Cu, Mo, Pd, Rh |
| 90° C. | Co, Er, Eu, Fe, Gd, Mn, Zn |
| 110° C. | Bi, Cr, Ni, Pb, Y |
| 130° C. | In, Mg |
| 150° C. | Sr |

The foregoing description of certain embodiments of the invention have been presented for purposes of illustration and description, and are not intended to be exhaustive or to limit the invention to the precise forms disclosed. The descriptions were selected to best explain the principles of the invention and their practical application to enable others skilled in the art to best utilize the invention in various embodiments and various modifications as are suited to the particular use contemplated. It is intended the scope of the invention not be limited by the specification, but be defined by the claims set forth below.

What is claimed is:

1. A sol-gel precursor comprising a cross-linkable molecule including a first metal $M_1$, wherein the first metal is directly bonded to carbon and the cross-linkable molecule is further conjugated to a first functional group capable of being conjugated to the first metal $M_1$, and a second functional group comprising a carboxylate group and a side chain R selected from a benzyl group, methyl group, ethyl group, propyl group, and butyl group that is a substituent on a carbon in the alpha position to the carbonyl carbon, wherein at least one of the oxygen atoms in the carboxylate group is ligated to a second metal $M_2$ selected from the group consisting of Ag, Bi, Co, Cr, Cu, Er, Eu, Gd, In, Mn, Mo, Pb, Pd, Pt, Rh, Y, Zn, B, Si, Ge, As, Sb, Te, and Po, and wherein the first metal $M_1$ is a semimetal selected from the group consisting of Bi, Si, Ge, and Sb.

2. The sol-gel precursor of claim 1, wherein the second metal $M_2$ is any metal selected from the group consisting of Ag, Co, Cr, Cu, Er, Eu, Gd, In, Mn, Mo, Pb, Pd, Pt, Rh, Y, and Zn.

3. The sol-gel precursor of claim 1, wherein the second metal $M_2$ is a semi-metal selected from the group consisting of Bi, Si, Ge, As, Sb and Te.

4. The sol-gel precursor of claim 1, wherein the functional group capable of being conjugated to the first metal $M_1$, and the second functional group comprising the carboxylate group and the side chain R together form a compound selected from the group consisting of organic compounds, bioorganic compounds and organometallic compounds.

5. The sol-gel precursor of claim 4, wherein the organic compound is selected from the group consisting of carboxylic acids, hydroxy acids, azide acids, isocyanate acids, isothiocyanate acids, thiol acids, maleimide acids and aldehyde acids.

6. The sol-gel precursor of claim 4, wherein the organic compound is a polyester.

7. The sol-gel precursor of claim 4, wherein the bioorganic compound is selected from the group consisting of amino acids, peptides and peptide fragments.

8. The sol-gel precursor of claim 4, wherein the side chain R is sterically hindering.

9. The sol-gel precursor of claim 4, wherein the side chain R has a chiral portion.

10. The sol-gel precursor of claim 4, wherein the side chain R comprises one or more alkyl side-chains.

11. The sol-gel precursor of claim 10, wherein the alkyl side-chain comprises a benzyl, methyl, ethyl, butyl or t-butyl derivative.

12. The sol-gel precursor of claim 4, wherein the side chain R comprises a functional group.

13. The sol-gel precursor of claim 1, wherein the sol-gel precursor comprises C, H, N, O and S and the mass of C, H, N, O and S in said sol-gel precursor is between about 40% and 90% of the total mass of the sol-gel precursor.

14. The sol-gel precursor of claim 1, wherein the sol-gel precursor has the following structure:

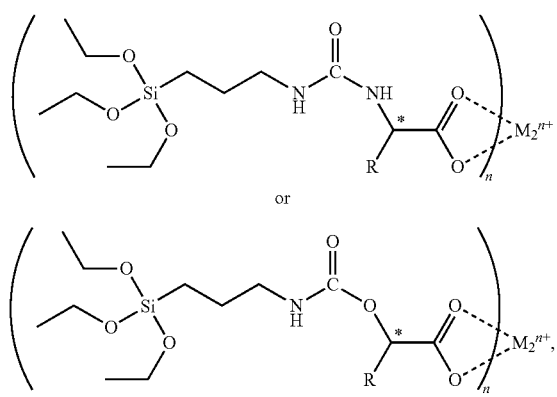

or wherein n+ is the oxidation state of $M_2$.

15. A sol-gel precursor comprising a cross-linkable molecule including a first metal $M_1$, wherein the first metal is directly bonded to carbon and the cross-linkable molecule is further conjugated to a first functional group capable of being conjugated to the first metal $M_1$, and a second functional group comprising a carboxylate group and a side chain R, wherein at least one of the oxygen atoms in the carboxylate group is ligated to a second metal $M_2$ selected from the group consisting of Bi, Si, Ge, As, Sb and Te.

16. The sol-gel precursor of claim 15, wherein the first metal $M_1$ is any metal on the periodic table.

17. The sol-gel precursor of claim 16, wherein the first metal $M_1$ is any metal selected from the group consisting of Ti, Al, Ga, Zn, Cd, Sn, Zr and Pb.

18. The sol-gel precursor of claim 16, wherein the first metal $M_1$ is a semimetal selected from the group consisting of Bi, Si, Ge, and Sb.

19. The sol-gel precursor of claim 15, wherein the functional group capable of being conjugated to the first metal $M_1$, and the second functional group comprising a carboxylate group and a side chain R together form a compound selected from the group consisting of organic compounds, bioorganic compounds and organometallic compounds.

20. The sol-gel precursor of claim 19, wherein the organic compound is selected from the group consisting of carboxylic acids, hydroxy acids, azide acids, isocyanate acids, isothiocyanate acids, thiol acids, maleimide acids and aldehyde acids.

21. The sol-gel precursor of claim 19, wherein the organic compound is a polyester.

22. The sol-gel precursor of claim 19, wherein the bioorganic compound is selected from the group consisting of amino acids, peptides and peptide fragments.

23. The sol-gel precursor of claim 15, wherein the side chain R is sterically hindering.

24. The sol-gel precursor of claim 15, wherein the side chain R has a chiral portion.

25. The sol-gel precursor of claim 15, wherein the side chain R comprises one or more alkyl side-chains.

26. The sol-gel precursor of claim 25, wherein the alkyl side-chain comprises a benzyl, methyl, ethyl, butyl or t-butyl derivative.

27. The sol-gel precursor of claim 15, wherein the side chain R comprises a functional group.

28. The sol-gel precursor of claim 27, wherein the functional group is selected from the group consisting of a therapeutic agent, a peptide, a polymer, an alcohol, an amine, a nanoparticle and a fluorescent dye.

29. The sol-gel precursor of claim 15, wherein the sol-gel precursor comprises C, H, N, O and S and the mass of C, H, N, O and S in said sol-gel precursor is between about 40% and 90% of the total mass of the sol-gel precursor.

30. The sol-gel precursor of claim 15, wherein the sol-gel precursor has the following structure:

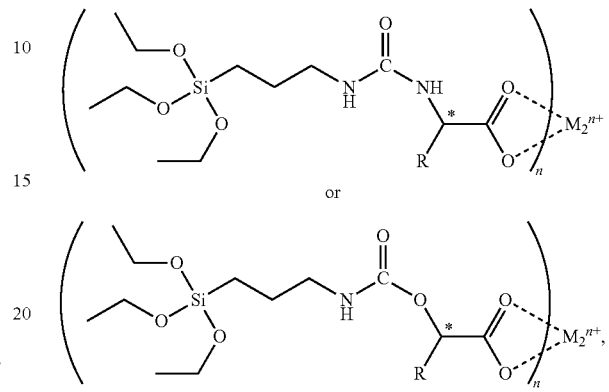

or wherein n+ is the oxidation state of $M_2$.

31. A sol-gel precursor comprising a cross-linkable molecule including a first metal $M_1$, wherein the first metal is directly bonded to carbon and the cross-linkable molecule is further conjugated to a first functional group capable of being conjugated to the first metal $M_1$, and a second functional group comprising a carboxylate group and a side chain R, wherein at least one of the oxygen atoms in the carboxylate group is ligated to a second metal $M_2$ that is a semimetal selected from the group consisting of Bi, Si, Ge, As, Sb, and Te,
    wherein the functional group capable of being conjugated to the first metal $M_1$, and the second functional group comprising a carboxylate group and a side chain R together form a polyester.

32. The sol-gel precursor of claim 31, wherein the first metal $M_1$ is any metal on the periodic table.

33. The sol-gel precursor of claim 32, wherein the first metal $M_1$ is any metal selected from the group consisting of Ti, Al, Ga, Zn, Cd, Sn, Zr and Pb.

34. The sol-gel precursor of claim 32, wherein the first metal $M_1$ is a semimetal selected from the group consisting of Bi, Si, Ge, and Sb.

35. A sol-gel precursor comprising a cross-linkable molecule including a first metal $M_1$, wherein the first metal is directly bonded to carbon and the cross-linkable molecule is further conjugated to a first functional group capable of being conjugated to the first metal $M_1$, and a second functional group comprising a carboxylate group and a side chain R, wherein at least one of the oxygen atoms in the carboxylate group is ligated to a second metal $M_2$ selected from the group consisting of Ag, Bi, Co, Cr, Cu, Er, Eu, Gd, In, Mn, Mo, Pb, Pd, Pt, Rh, Y, Zn, B, Si, Ge, As, Sb, Te, and Po, wherein the sol-gel precursor comprises C, H, N, O and S and the mass of C, H, N, O and S in said sol-gel precursor is between about 40% and 90% of the total mass of the sol-gel precursor, and wherein the first metal $M_1$ is a semimetal selected from the group consisting of Bi, Si, Ge, and Sb.

36. The sol-gel precursor of claim 35, wherein the second metal $M_2$ is any metal selected from the group consisting of Ag, Co, Cr, Cu, Er, Eu, Gd, In, Mn, Mo, Pb, Pd, Pt, Rh, Y, and Zn.

37. The sol-gel precursor of claim 35, wherein the second metal $M_2$ is a semi-metal selected from the group consisting of Bi, Si, Ge, As, Sb and Te.

38. The sol-gel precursor of claim 35, wherein the functional group capable of being conjugated to the first metal $M_1$, and the second functional group comprising a carboxylate group and a side chain R together form a compound selected from the group consisting of organic compounds, bioorganic compounds and organometallic compounds.

39. The sol-gel precursor of claim 38, wherein the organic compound is selected from the group consisting of carboxylic acids, hydroxy acids, azide acids, isocyanate acids, isothiocyanate acids, thiol acids, maleimide acids and aldehyde acids.

40. The sol-gel precursor of claim 38, wherein the organic compound is a polyester.

41. The sol-gel precursor of claim 38, wherein the bioorganic compound is selected from the group consisting of amino acids, peptides and peptide fragments.

42. The sol-gel precursor of claim 35, wherein the side chain R is sterically hindering.

43. The sol-gel precursor of claim 35, wherein the side chain R has a chiral portion.

44. The sol-gel precursor of claim 35, wherein the side chain R comprises one or more alkyl side-chains.

45. The sol-gel precursor of claim 44, wherein the alkyl side-chain comprises a benzyl, methyl, ethyl, butyl or t-butyl derivative.

46. The sol-gel precursor of claim 35, wherein the side chain R comprises a functional group.

47. The sol-gel precursor of claim 35, wherein the sol-gel precursor has the following structure:

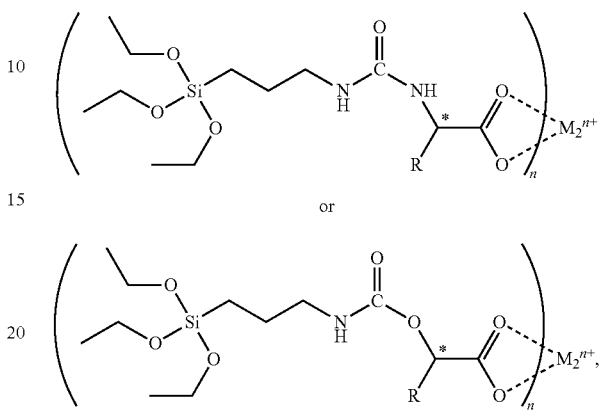

wherein n+ is the oxidation state of $M_2$.

* * * * *